(12) United States Patent
Thome et al.

(10) Patent No.: US 9,681,930 B2
(45) Date of Patent: Jun. 20, 2017

(54) IMPLANTS FOR ENHANCED ANCHORING WITHIN BONE

(71) Applicant: JJGC INDUSTRIA E COMERCIO DE MATERIAIS DENTARIOUS S/A, Curitiba (BR)

(72) Inventors: Geninho Thome, Curitiba (BR); Felix Andreas Mertin, Curitiba (BR); Alexsander Luiz Golin, Curitiba (BR); Ilderaldo Jose Lucca, Curitiba (BR)

(73) Assignee: JJGC INDUSTRIA E COMERCIO DE MATERIAIS DENTARIOUS S/A, Curitiba (BR)

( * ) Notice: Subject to any disclaimer, the term of this patent is extended or adjusted under 35 U.S.C. 154(b) by 0 days.

(21) Appl. No.: 14/874,145

(22) Filed: Oct. 2, 2015

(65) Prior Publication Data

US 2016/0166358 A1    Jun. 16, 2016

(30) Foreign Application Priority Data

Dec. 15, 2014 (BR) .............................. 102014031426

(51) Int. Cl.
A61C 8/00        (2006.01)
(52) U.S. Cl.
CPC ............ *A61C 8/0025* (2013.01); *A61C 8/006* (2013.01); *A61C 8/0037* (2013.01); *A61C 8/0069* (2013.01); *A61C 8/0075* (2013.01)
(58) Field of Classification Search
CPC ..... A61C 8/0037; A61C 8/006; A61C 8/0071; A61C 8/0069; A61C 8/007; A61C 8/0025; A61C 8/0024; A61C 8/0022
See application file for complete search history.

(56) References Cited

U.S. PATENT DOCUMENTS

| 422,307 A | 2/1890 | Libbey |
| 1,698,951 A | 1/1929 | Holmes |

(Continued)

FOREIGN PATENT DOCUMENTS

| BR | MU8801468 U2 | 11/2009 |
| BR | PI0902500 A2 | 4/2011 |

(Continued)

OTHER PUBLICATIONS

International Search Report and Written Opinion dated Jan. 8, 2016 in Int'l PCT Patent Application Serial No. PCT/BR2015/050240.

(Continued)

*Primary Examiner* — Nicholas Lucchesi
*Assistant Examiner* — Shannel Wright
(74) *Attorney, Agent, or Firm* — Foley & Lardner LLP; Christopher C. Bolten

(57) ABSTRACT

Implants for anchoring within bone are provided herein. An implant may include at least one thread extending around a core in a plurality of turns from the coronal region to the apical region. The thread(s) has a thread outer diameter that may define a cylindrical portion, wherein the thread outer diameter remains constant for more than one turn around the core, and define a conical portion, wherein the thread outer diameter decreases at a thread diameter decrease rate in the apical direction. The thread(s) may have a plurality of notches spaced radially and longitudinally from one another. The notches may be partially notched to reflect a portion of a semi-spherical surface and partially notched to reflect a portion of a semi-cylindrical surface.

22 Claims, 9 Drawing Sheets

(56) References Cited

U.S. PATENT DOCUMENTS

| | | |
|---|---|---|
| 2,215,770 A | 9/1940 | Sheffield |
| 2,788,046 A | 4/1957 | Rosan |
| 3,481,380 A | 12/1969 | Breed |
| 3,672,058 A | 6/1972 | Nikoghossian |
| 3,797,113 A | 3/1974 | Brainin |
| 3,849,887 A | 11/1974 | Brainin |
| 4,103,422 A | 8/1978 | Weiss et al. |
| 4,144,795 A | 3/1979 | Gutshall |
| 4,293,302 A | 10/1981 | Hassler et al. |
| 4,406,623 A | 9/1983 | Grafelmann et al. |
| 4,431,416 A | 2/1984 | Niznick |
| 4,468,200 A | 8/1984 | Munch |
| 4,531,915 A | 7/1985 | Tatum, Jr. |
| 4,547,157 A | 10/1985 | Driskell |
| 4,645,453 A | 2/1987 | Niznick |
| 4,713,003 A | 12/1987 | Symington et al. |
| 4,723,913 A | 2/1988 | Bergman |
| 4,738,623 A | 4/1988 | Driskell |
| 4,758,161 A | 7/1988 | Niznick |
| 4,826,434 A | 5/1989 | Krueger |
| 4,863,383 A * | 9/1989 | Grafelmann ....... A61B 17/8625 433/174 |
| 4,865,603 A | 9/1989 | Noiles |
| 4,932,868 A | 6/1990 | Linkow et al. |
| 4,960,381 A | 10/1990 | Niznick |
| 4,976,739 A | 12/1990 | Duthie, Jr. |
| 5,000,686 A | 3/1991 | Lazzara et al. |
| 5,002,488 A | 3/1991 | Homsy |
| 5,007,835 A | 4/1991 | Valen |
| 5,061,181 A | 10/1991 | Niznick |
| 5,062,800 A | 11/1991 | Niznick |
| 5,071,350 A | 12/1991 | Niznick |
| 5,074,790 A | 12/1991 | Bauer |
| 5,076,788 A | 12/1991 | Niznick |
| RE33,796 E | 1/1992 | Niznick |
| 5,078,607 A | 1/1992 | Niznick |
| 5,087,201 A | 2/1992 | Mondani et al. |
| 5,095,817 A | 3/1992 | Takamura |
| 5,120,171 A | 6/1992 | Lasner |
| 5,194,000 A | 3/1993 | Dury |
| 5,195,892 A | 3/1993 | Gersberg |
| 5,226,766 A | 7/1993 | Lasner |
| 5,230,590 A | 7/1993 | Bohannan et al. |
| 5,328,371 A | 7/1994 | Hund et al. |
| 5,343,391 A | 8/1994 | Mushabac |
| 5,427,527 A | 6/1995 | Niznick et al. |
| 5,433,606 A | 7/1995 | Niznick et al. |
| 5,435,723 A | 7/1995 | O'Brien |
| 5,439,381 A | 8/1995 | Cohen |
| 5,484,286 A | 1/1996 | Hansson |
| 5,527,183 A | 6/1996 | O'Brien |
| 5,571,017 A | 11/1996 | Niznick |
| 5,580,246 A | 12/1996 | Fried et al. |
| 5,584,629 A | 12/1996 | Bailey et al. |
| 5,588,838 A | 12/1996 | Hansson et al. |
| 5,593,410 A | 1/1997 | Vrespa |
| 5,601,429 A | 2/1997 | Blacklock |
| 5,628,630 A | 5/1997 | Misch et al. |
| 5,639,237 A | 6/1997 | Fontenot |
| 5,642,996 A | 7/1997 | Mochida et al. |
| 5,645,740 A | 7/1997 | Naiman et al. |
| 5,674,072 A | 10/1997 | Moser et al. |
| 5,702,445 A | 12/1997 | Branemark |
| 5,716,412 A | 2/1998 | DeCarlo et al. |
| 5,725,375 A | 3/1998 | Rogers |
| 5,727,943 A | 3/1998 | Beaty et al. |
| 5,733,123 A | 3/1998 | Blacklock et al. |
| 5,752,830 A | 5/1998 | Suarez |
| 5,759,034 A | 6/1998 | Daftary |
| 5,782,918 A | 7/1998 | Klardie et al. |
| 5,795,160 A | 8/1998 | Hahn et al. |
| 5,810,589 A | 9/1998 | Michnick et al. |
| 5,810,590 A | 9/1998 | Fried et al. |
| 5,816,812 A | 10/1998 | Kownacki et al. |
| 5,820,374 A | 10/1998 | Simmons et al. |
| 5,823,776 A | 10/1998 | Duerr et al. |
| 5,823,777 A | 10/1998 | Misch et al. |
| 5,858,079 A | 1/1999 | Ohtsu et al. |
| 5,868,747 A | 2/1999 | Ochoa et al. |
| 5,871,356 A | 2/1999 | Guedj |
| 5,876,453 A | 3/1999 | Beaty |
| 5,897,319 A | 4/1999 | Wagner et al. |
| 5,915,968 A | 6/1999 | Kirsch et al. |
| 5,931,675 A | 8/1999 | Callan |
| 5,938,444 A | 8/1999 | Hansson et al. |
| 5,954,504 A | 9/1999 | Misch et al. |
| 5,964,768 A | 10/1999 | Huebner |
| 5,967,783 A | 10/1999 | Ura |
| 6,039,568 A | 3/2000 | Hinds |
| 6,048,204 A | 4/2000 | Klardie et al. |
| 6,068,479 A | 5/2000 | Kwan |
| 6,116,904 A | 9/2000 | Kirsch et al. |
| 6,129,730 A | 10/2000 | Bono et al. |
| 6,135,772 A * | 10/2000 | Jones ..................... A61C 8/00 433/174 |
| 6,149,432 A | 11/2000 | Shaw et al. |
| 6,168,633 B1 | 1/2001 | Shoher et al. |
| 6,200,345 B1 | 3/2001 | Morgan |
| 6,227,857 B1 | 5/2001 | Morgan et al. |
| 6,227,859 B1 | 5/2001 | Sutter |
| 6,273,722 B1 | 8/2001 | Phillips |
| 6,283,754 B1 | 9/2001 | Wohrle |
| 6,287,117 B1 | 9/2001 | Niznick |
| 6,312,259 B1 * | 11/2001 | Kvarnstrom ......... A61C 8/0075 433/173 |
| 6,315,564 B1 | 11/2001 | Levisman |
| 6,364,663 B1 | 4/2002 | Dinkelacker |
| 6,371,709 B1 | 4/2002 | Papafotiou et al. |
| 6,394,806 B1 | 5/2002 | Kumar |
| 6,398,786 B1 | 6/2002 | Sesic |
| 6,402,515 B1 | 6/2002 | Palti et al. |
| 6,419,491 B1 | 7/2002 | Ricci et al. |
| 6,431,869 B1 | 8/2002 | Reams et al. |
| 6,481,760 B1 * | 11/2002 | Noel ..................... E21B 17/042 411/311 |
| 6,482,076 B1 | 11/2002 | Straub et al. |
| 6,527,554 B2 * | 3/2003 | Hurson ............... A61C 8/0006 433/173 |
| 6,547,564 B1 | 4/2003 | Hansson |
| 6,626,671 B2 | 9/2003 | Klardie et al. |
| 6,648,643 B2 | 11/2003 | Hollander et al. |
| 6,655,961 B2 | 12/2003 | Cottrell |
| 6,655,962 B1 | 12/2003 | Kennard |
| 6,667,701 B1 | 12/2003 | Tao |
| 6,726,481 B1 | 4/2004 | Zickmann et al. |
| 6,726,689 B2 | 4/2004 | Jackson |
| 6,733,291 B1 | 5/2004 | Hurson |
| 6,733,503 B2 | 5/2004 | Layrolle et al. |
| 6,769,913 B2 | 8/2004 | Hurson |
| 6,840,769 B2 | 1/2005 | Augthun et al. |
| 6,846,180 B1 | 1/2005 | Joos |
| 6,887,077 B2 | 5/2005 | Porter et al. |
| 6,896,517 B1 | 5/2005 | Bjorn et al. |
| 6,913,465 B2 | 7/2005 | Howlett et al. |
| 6,955,258 B2 | 10/2005 | Howlett et al. |
| 6,981,873 B2 | 1/2006 | Choi et al. |
| 6,997,711 B2 | 2/2006 | Miller |
| 7,008,227 B2 | 3/2006 | Carmichael et al. |
| 7,014,464 B2 | 3/2006 | Niznick |
| 7,108,510 B2 | 9/2006 | Niznick |
| 7,198,488 B2 * | 4/2007 | Lang ................. A61B 17/1615 433/174 |
| 7,207,800 B1 | 4/2007 | Kwan |
| 7,210,933 B2 | 5/2007 | Haessler |
| 7,249,949 B2 | 7/2007 | Carter |
| 7,273,373 B2 | 9/2007 | Horiuchi |
| 7,281,925 B2 | 10/2007 | Hall |
| 7,341,454 B2 | 3/2008 | Balfour et al. |
| 7,377,781 B1 | 5/2008 | Karapetyan |
| 7,383,163 B2 | 6/2008 | Holberg |
| 7,677,891 B2 * | 3/2010 | Niznick ............... A61C 8/0025 433/174 |
| 7,806,693 B2 * | 10/2010 | Hurson ............... A61C 8/0025 433/174 |

(56) References Cited

U.S. PATENT DOCUMENTS

| | | | |
|---|---|---|---|
| 8,016,594 B2 | 9/2011 | Ferris et al. | |
| 8,029,285 B2 | 10/2011 | Holmen et al. | |
| 8,066,511 B2 | 11/2011 | Wohrle et al. | |
| 8,083,442 B2 | 12/2011 | Pan | |
| 8,192,199 B2 | 6/2012 | Arni | |
| 8,221,119 B1* | 7/2012 | Valen | A61C 8/0025 433/174 |
| 8,277,218 B2 | 10/2012 | D'Alise | |
| 8,408,904 B2 | 4/2013 | Purga et al. | |
| 8,485,819 B2 | 7/2013 | Callan | |
| 8,491,302 B2 | 7/2013 | Arni | |
| 8,714,977 B2 | 5/2014 | Fromovich et al. | |
| 8,758,012 B2* | 6/2014 | Hurson | A61C 8/0018 433/173 |
| 8,764,443 B2 | 7/2014 | Hall | |
| 8,858,230 B2* | 10/2014 | Hsieh | A61C 8/0025 433/174 |
| 8,870,573 B2* | 10/2014 | Hung | A61C 8/0039 433/174 |
| 9,220,582 B2 | 12/2015 | Thome et al. | |
| 2001/0000748 A1 | 5/2001 | Rogers et al. | |
| 2002/0064758 A1 | 5/2002 | Lee | |
| 2002/0102518 A1 | 8/2002 | Mena | |
| 2002/0106612 A1 | 8/2002 | Back et al. | |
| 2002/0177106 A1 | 11/2002 | May et al. | |
| 2003/0064349 A1 | 4/2003 | Simmons | |
| 2003/0124487 A1 | 7/2003 | McDevitt | |
| 2004/0006346 A1 | 1/2004 | Holmen et al. | |
| 2004/0033469 A1* | 2/2004 | Blacklock | A61C 8/0022 433/173 |
| 2004/0063069 A1 | 4/2004 | Lombardi | |
| 2004/0063071 A1* | 4/2004 | Schroering | A61C 8/0022 433/174 |
| 2005/0053897 A1 | 3/2005 | Wu | |
| 2005/0100863 A1 | 5/2005 | Chang | |
| 2005/0214714 A1 | 9/2005 | Wohrle | |
| 2005/0244789 A1 | 11/2005 | Crohin et al. | |
| 2005/0260540 A1 | 11/2005 | Hall | |
| 2005/0266381 A1 | 12/2005 | Abarno | |
| 2005/0287497 A1 | 12/2005 | Carter | |
| 2006/0003290 A1 | 1/2006 | Niznick | |
| 2006/0078847 A1 | 4/2006 | Kwan | |
| 2006/0099153 A1 | 5/2006 | Kato et al. | |
| 2006/0147880 A1 | 7/2006 | Krumsiek et al. | |
| 2006/0172257 A1* | 8/2006 | Niznick | A61C 8/0022 433/173 |
| 2006/0172258 A1* | 8/2006 | Niznick | A61C 8/0025 433/174 |
| 2006/0183078 A1 | 8/2006 | Niznick | |
| 2006/0223030 A1 | 10/2006 | Dinkelacker | |
| 2007/0065778 A1 | 3/2007 | Lippe | |
| 2007/0287128 A1* | 12/2007 | Claudio | A61C 8/0022 433/173 |
| 2008/0014556 A1 | 1/2008 | Neumeyer | |
| 2008/0032264 A1 | 2/2008 | Hall | |
| 2008/0182227 A1 | 7/2008 | Wolf et al. | |
| 2008/0187886 A1 | 8/2008 | Robb | |
| 2008/0293014 A1 | 11/2008 | Chung | |
| 2009/0220914 A1 | 9/2009 | Gershenzon | |
| 2009/0233256 A1 | 9/2009 | Schroering | |
| 2009/0305191 A1* | 12/2009 | Jandali | A61C 8/0089 433/174 |
| 2010/0092920 A1 | 4/2010 | Hsieh | |
| 2010/0190138 A1* | 7/2010 | Giorno | A61C 8/0022 433/174 |
| 2011/0027756 A1 | 2/2011 | Benatouil et al. | |
| 2011/0097689 A1 | 4/2011 | Thome | |
| 2011/0117522 A1 | 5/2011 | Verma et al. | |
| 2011/0123953 A1 | 5/2011 | Jorneus et al. | |
| 2011/0143317 A1 | 6/2011 | Thome | |
| 2011/0244427 A1* | 10/2011 | Hung | A61C 8/0039 433/174 |
| 2011/0294094 A1* | 12/2011 | Moshavi | A61C 8/0022 433/174 |
| 2012/0077151 A1* | 3/2012 | Nary Filho | A61C 8/0071 433/174 |
| 2012/0135378 A1 | 5/2012 | Thome | |
| 2012/0156647 A1 | 6/2012 | Yoon et al. | |
| 2012/0178048 A1* | 7/2012 | Cottrell | A61C 8/0025 433/174 |
| 2012/0237898 A1 | 9/2012 | Palti et al. | |
| 2012/0237899 A1 | 9/2012 | Holmstrom et al. | |
| 2012/0237900 A1 | 9/2012 | Lancieux et al. | |
| 2012/0288824 A1 | 11/2012 | Nordin et al. | |
| 2013/0045144 A1 | 2/2013 | Perozziello et al. | |
| 2013/0177874 A1* | 7/2013 | Hori | A61C 8/0024 433/174 |
| 2013/0224687 A1 | 8/2013 | Karmon | |
| 2013/0260339 A1 | 10/2013 | Reddy et al. | |
| 2013/0273500 A1* | 10/2013 | Giorno | A61C 8/0024 433/174 |
| 2013/0309630 A1 | 11/2013 | Bolleter | |
| 2014/0045144 A1* | 2/2014 | Dukhan | A61C 8/0025 433/174 |
| 2014/0186799 A1* | 7/2014 | Pan | A61C 8/0025 433/174 |
| 2014/0234800 A1* | 8/2014 | Laster | A61C 8/0039 433/174 |
| 2015/0044638 A1* | 2/2015 | Baez | A61C 8/0025 433/174 |
| 2015/0111175 A1 | 4/2015 | Thome et al. | |
| 2015/0230889 A1* | 8/2015 | Kim | A61C 8/0037 433/174 |
| 2015/0297321 A1* | 10/2015 | Chen | A61C 8/0025 433/174 |

FOREIGN PATENT DOCUMENTS

| | | | | |
|---|---|---|---|---|
| CH | 2145600 A1 * | 1/2010 | | A61C 8/0022 |
| CN | WO 2012075614 A1 * | 6/2012 | | A61C 8/0018 |
| CN | 203029412 U | 7/2013 | | |
| DE | 39 04 528 A1 | 8/1990 | | |
| DE | 102 31 743 A1 | 2/2004 | | |
| EP | 0 707 835 A1 | 4/1996 | | |
| EP | 0 819 410 A1 | 1/1998 | | |
| EP | 0 895 757 A1 | 2/1999 | | |
| EP | 1 396 236 A1 | 3/2004 | | |
| EP | 1 728 486 A1 | 12/2006 | | |
| FR | 2600246 A1 | 12/1987 | | |
| FR | 2610512 A1 | 8/1988 | | |
| JP | H08-19555 A | 1/1996 | | |
| RU | 2190373 C1 | 10/2002 | | |
| RU | 2202982 C1 | 4/2003 | | |
| WO | WO-01/49199 A2 | 7/2001 | | |
| WO | WO-03/005928 A1 | 1/2003 | | |
| WO | WO-2006/026938 A1 | 3/2006 | | |
| WO | WO-2006/082050 A1 | 8/2006 | | |
| WO | WO-2007/091997 A1 | 8/2007 | | |
| WO | WO-2008/096294 A1 | 8/2008 | | |
| WO | WO-2008/157137 A1 | 12/2008 | | |
| WO | WO-2009/007891 A1 | 1/2009 | | |
| WO | WO-2009/054005 A2 | 4/2009 | | |
| WO | WO-2009/130415 A2 | 10/2009 | | |
| WO | WO-2011/083400 A2 | 7/2011 | | |
| WO | WO-2011/132007 A2 | 10/2011 | | |
| WO | WO-2012/007118 A1 | 1/2012 | | |
| WO | WO-2012/059908 A1 | 5/2012 | | |
| WO | WO-2012/123661 A1 | 9/2012 | | |
| WO | WO-2012/126466 A1 | 9/2012 | | |
| WO | WO-2013/004703 A1 | 1/2013 | | |
| WO | WO-2013/068088 A1 | 5/2013 | | |
| WO | WO-2006/094997 A1 | 6/2016 | | |

OTHER PUBLICATIONS

U.S. Appl. No. 29/530,135, filed Jun. 12, 2015, Thome, et al.
ADIN Dental Implant Systems, Tourag (TM)-S, Website Catalog, 2 pages, Sep. 14, 2014.
AlphaBio Product Catalog, 16 pages (1995).
AlphaBio System Product Catalog, 53 pages, Mar. 2003.

(56) References Cited

OTHER PUBLICATIONS

Anthogyr Implants SAS Catalog, The Implantology Serenly, 40 pages (2002).
Bicon Dental Implants Catalog, 7 pages (1997).
Hansson, The Implant Neck: Smooth or Provided With Retention Elements, A Biomechanical Approach, Clin. Oral Impl. Res, 10:394-405 (1999).
Instradent Catalog—"Facility Implants—The Solution for Narrow Restorative Spaces", 4 pages (2014).
Instradent Catalog—"Neodent—20 Years of Advancement in Implantology", 8 pages (2013).
Instradent Catalog—"One Step Hybrid—The Definitive Solution For The Immediate Loading of a Full Arch Prosthesis", 8 pages (2014).
Instradent Catalog—"The CM Implant Line", 8 pages (2013).
Instradent Catalog—"The CM Implant Line—Overview", 2 pages (2013).
Instradent Catalog—"The Smart Implant Line—External Hex—Overview", 2 pages (2013).
Instradent Catalog—"The Smart Implant Line—External Hex, A Classic in Versatility", 8 pages (2013).
Instradent Catalog—"The WS Implant Line—Overview", 2 pages (2013).
Judy, et al., Improved Technique of endodontic stabilization—biofunctional considerations, Oral Health, vol. 65, No. 4, pp. 36-44 (1975).
Ledermann, et al., Long-Lasting Osseointegration of Immediately Loaded, Bar-Connected TPS Screws After 12 Years of Function: A Histologic Case Report of a 95-year-old Patient, The International Journal of Periodontics & Restorative Dentistry, 18(6):553-563 (1998).
Ledermann, et al., Titanium-Coated Screw Implants as Alloplastic Endosteal Retention Element in the Edentulous Problematic Mandible (I), Systematic Procedure to the Time of Impression-Taking, Color Atlas, Quintessence International, pp. 895-901 (1981).
M Implant—Double Morse Taper Connection, http://en.tbr-implants.com/home/products/implants/implant-m, 3 pages, Sep. 2014.
Spiekermann, et al., Color Atlas of Dental Medicine, Implantology, Ledermann Screw Implant, p. 52, (1995).
SwissPlus Implant System—Product Catalog, "Centerpulse", 28 pages (2003).
Tapered SwissPlus Self-Tapping Design & Double Lead Threads, Zimmer Dental, http://www.zimmerdental.com/products/implants/im_tswpFSelfTap.aspx, 1 page, (2014).
Weiss, Charles M., DDS, Principles and Practice of Implant Dentistry, Chapter 19—Endodontic Stabilizer Implants—Tooth Root Extension for Improved Prognosis, 17 pages (2001).

\* cited by examiner

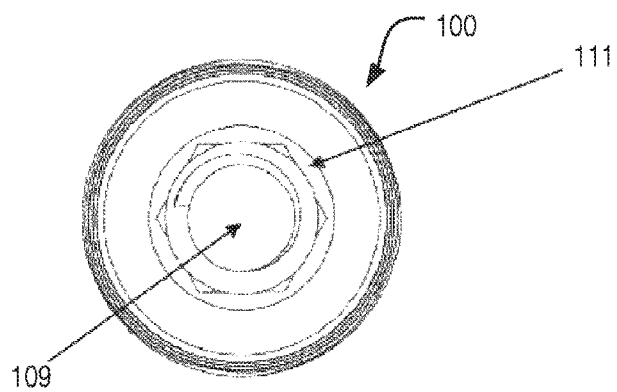
FIG. 1G
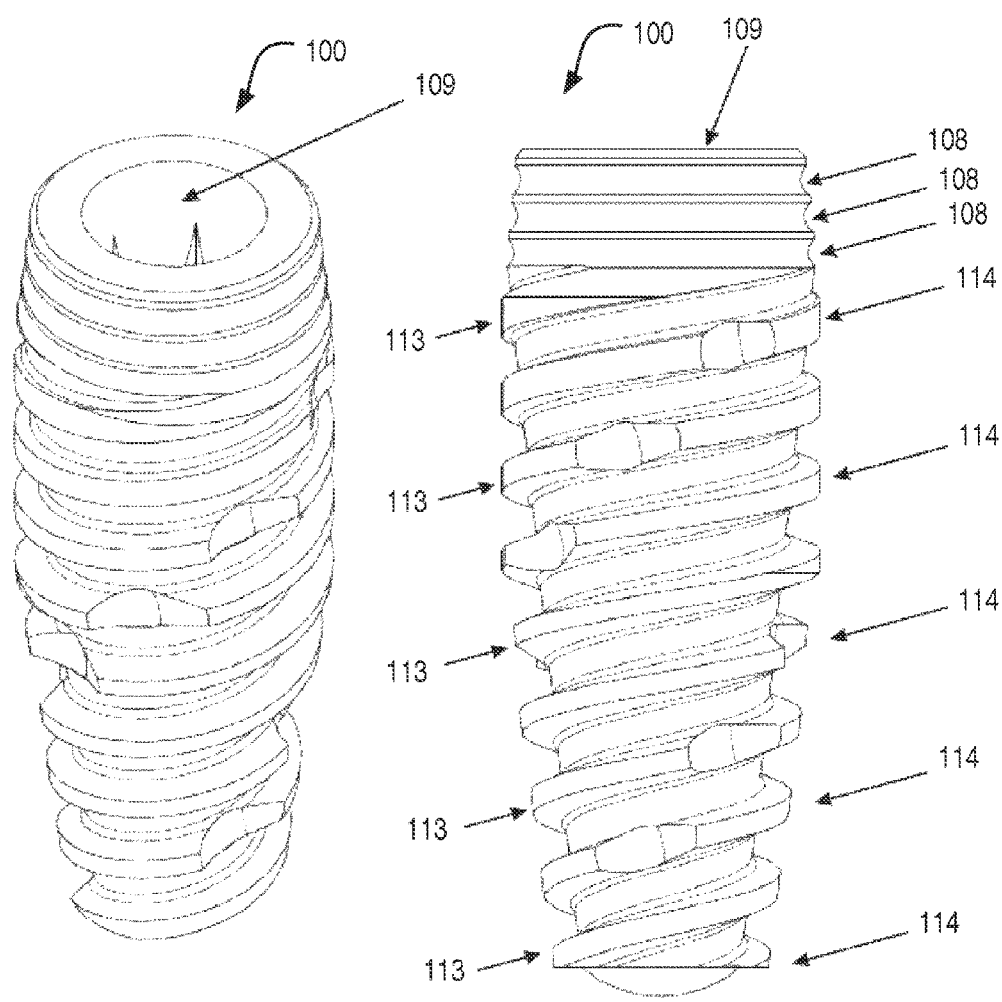
FIG. 1H
FIG. 1I

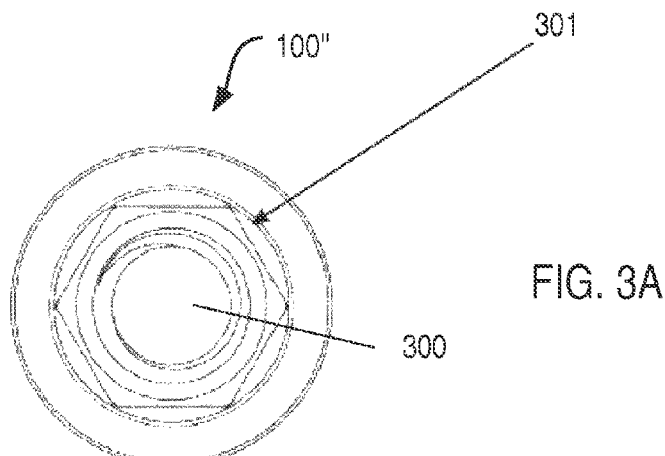
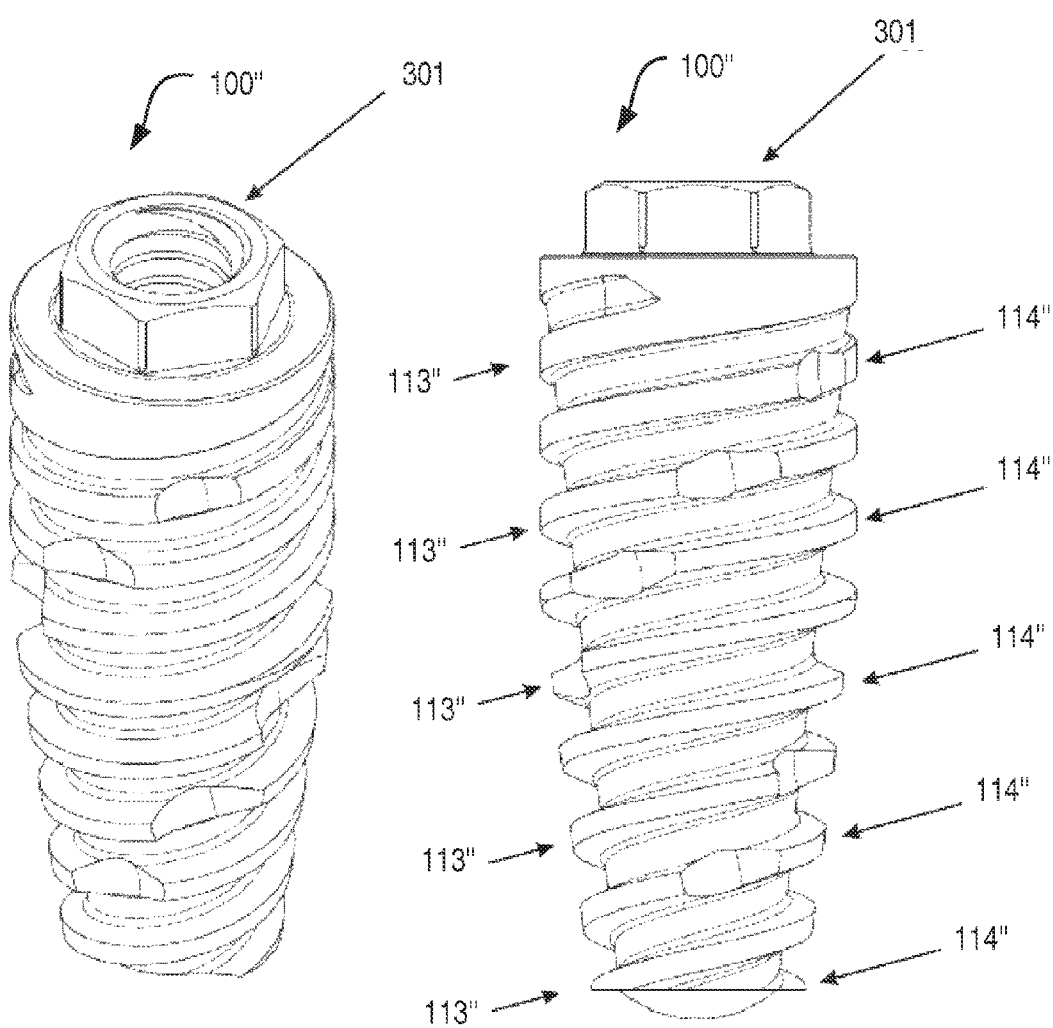
FIG. 3A
FIG. 3B    FIG. 3C

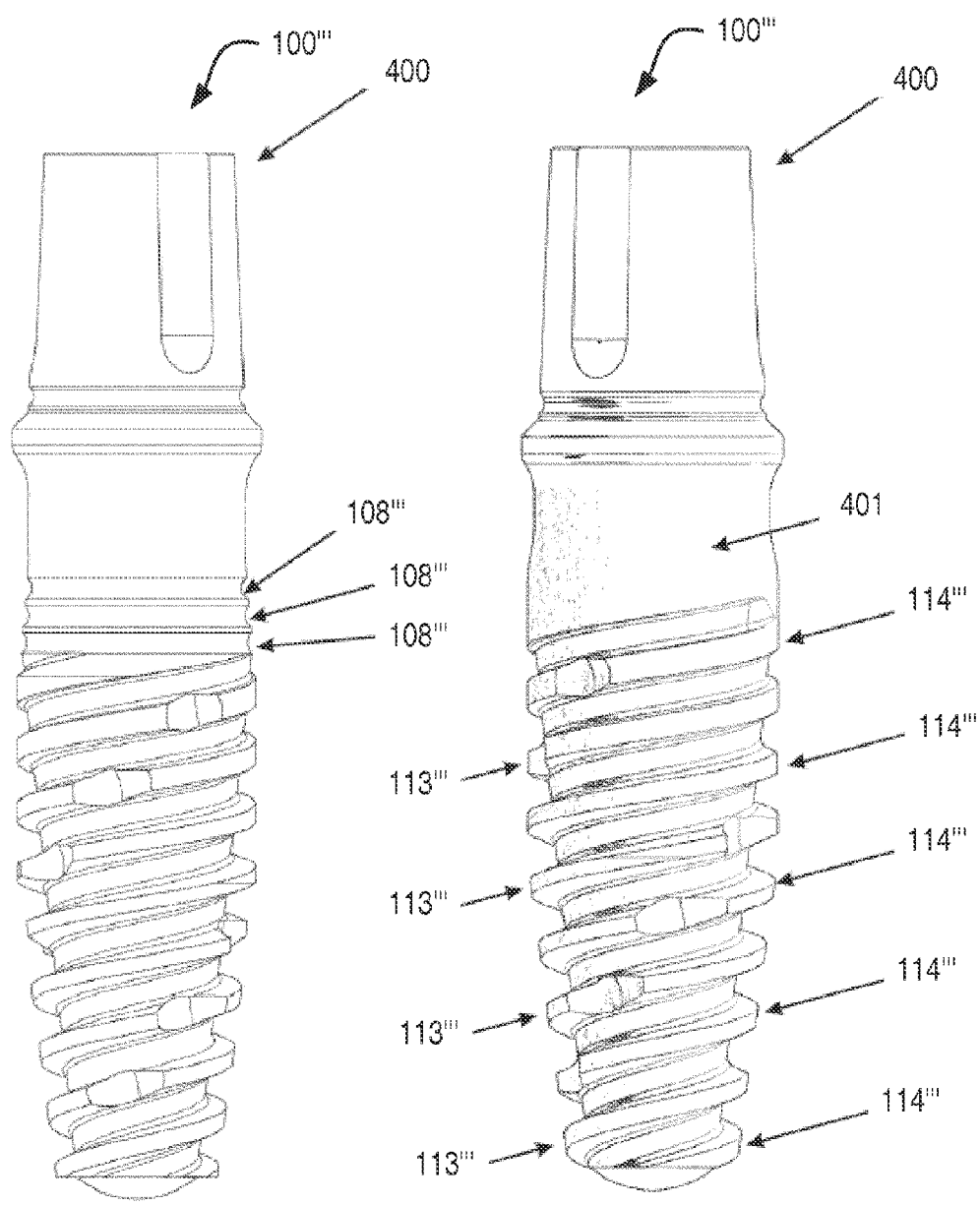

IMPLANTS FOR ENHANCED ANCHORING WITHIN BONE

I. CROSS-REFERENCE TO RELATED APPLICATIONS

This application claims the benefit of priority to Brazilian Patent Application No. 10 2014 031426 1, filed Dec. 15, 2014, the entire contents of which are incorporated herein by reference.

II. TECHNICAL FIELD

This technology generally relates to implants for anchoring within bone, such as Osseointegrated dental implants.

III. BACKGROUND

Osseointegrated implants may be used to anchor prosthetic structures, bone substitutes, or corrective elements on the human skeleton. For example, dental and orthopedic Osseointegrated implants in the form of screws may be anchored to the jawbone via the mouth to support prosthetic substitutes for one or more missing, lost, removed, or damaged teeth. As another example, screw implants may be installed on the spinal column for the fixation of bars to support and space vertebrae.

Bones are generally made of a rigid outer layer and a vascularized spongy core. The thickness of each of these rigid and spongy regions is particular to the biology of each person. During installation of an implant, however, it is expected that part of the implant will remain in the rigid region and part in the spongy region. To increase the stability of the implant after installation, and to reduce the patient's healing time, both the amount of bone removed and the damage to the blood vessels in proximity to the implant should be minimized during installation.

Most implants available on the market are formed of a cylindrical, generally screw-shaped body adapted for insertion into the bone. The cylinder is usually made from a biocompatible metal, such as titanium and alloys thereof, and may be coated with other types of biocompatible materials, such as hydroxyapatite, and/or receive a surface treatment in order to improve the osseointegration quality of the surface.

The different implants often diverge in the characteristics and geometry of their threads, as persons in the art seek to improve the quality of implant engagement with the bone structure.

U.S. Pat. No. 8,029,285 to Holman describes an implant generally in the form of a threaded cylinder having a prosthetic interface at its upper end, also known as the coronal end. At the lower end of the implant, also known as the apical end, there is a cut that runs through multiple threads, forming a self-tapping structure. Upon inserting implants with this type of structure, the lower part tends to accumulate bone material, which makes it difficult for the cut material to exit, leading to a loss of the self-tapping effect. The same implant further includes a slight increase in the diameter of the cylindrical body in the coronal region. Such increase is intended to compress the rigid region of the bone at the final moment when installing the implant, with the intention of increasing stability after installation. There are significant drawbacks to use of the implant designs in Holman such as the accumulation of material and fluids in the bone cavity during the installation of the implant that can lead to osseointegration issues, resulting in extended healing time.

There have been attempts to reduce such accumulation of material and fluids in bone during installation. For example, EP 0 895 757 B1 to Corigliani describes providing drainage channels along with a body whose core to gradually compress the bone without retaining fluids.

U.S. Pat. No. 8,714,977 to Fromovich describes a dental implant that facilitates insertion including a body having a coronal end and an apical end opposite the coronal end. An implant-prosthetic interface region is provided adjacent the coronal end. A tapered region is adjacent the apical end. A variable profile helical thread extends along the tapered region. The thread becomes broader in the apical-coronal direction and higher in the coronal-apical direction. The threads include an apical side, a coronal side and a lateral edge connecting them. The variable profile thread includes an expanding length of the lateral edge while the distance of the lateral edge from the base is reduced in the direction of the coronal end. The implant also has a gradual compressing tapered core, a self-drilling apical end with a spiral tap, and a coronal end with and inverse tapering.

The use of a conical core permits insertion of the implant into a bore of smaller diameter, which will be widened during the insertion, preserving a larger amount of bone around the implant. The conical core further has the advantage of compressing the bone during installation, increasing the stability after insertion thereof. However, the use of wide threads makes it difficult to align the implant in the bore at the initial moment of insertion, which may call for adjustment during insertion leading to the undesirable result of increased bone loss. Excessively wide threads from conventional designs also may cause problems when the space for insertion of the implant is limited by the roots of adjacent teeth—especially in the molar region, where roots extend sideways, and cutting the root of a healthy tooth with the implant thread would damage, and may even lead to the loss of, the tooth. Furthermore, a wide thread cuts a larger amount of the vascularization around the implant region, which delays healing.

Additionally, the continuously cut self-tapping structure concentrated in the apical portion of conventional implants suffers from drawbacks of accumulation of material within the self-tapping structure, increasing risks of osseointegration issues leading to extended healing time.

IV. SUMMARY

Implants are provided herein that are designed to minimize bone loss during installation as compared to conventional implants. The implants facilitate proper orientation during installation and minimize damage to the blood vessels surrounding the implant region, while improving the stability of the implant after installation. The implants provided herein may include a self-drilling thread geometry that distributes bone removal structure along the length of the implant with radially spaced-apart curved cut cavities. The implants also may have a high diameter-profile configuration, which provides the greatest thread width in the central region (e.g., about midway point of implant, within 10% of the midway point of implant, within 20% of the midway point of implant, within 30% of the midway point of implant) of the implant lengthwise and the thread width need not increase thereafter in the coronal direction.

In accordance with one aspect, an implant for anchoring within bone (e.g., jawbone) is provided. The implant may include a coronal region having a coronal end and an apical region having an apical end, the apical end opposite the coronal end. The implant also may have a core, a prosthetic interface, and at least one thread. The core may extend from the coronal region to the apical region. The core may have a core outer diameter that decreases at a core diameter decrease rate in an apical direction towards the apical end. The prosthetic interface is preferably at the coronal region (e.g., partially or fully). The at least one thread may extend around the core in a plurality of turns from the coronal region to the apical region. The at least one thread has a thread outer diameter that may be configured to define a cylindrical portion, wherein the thread outer diameter remains constant for more than one turn around the core, and to define a conical portion, wherein the thread outer diameter decreases at a thread diameter decrease rate in the apical direction. The thread diameter decrease rate may be greater than the core diameter decrease rate.

The cylindrical portion and the conical portion may meet at an inflection point. The thread height of the at least one thread may be greater at turns adjacent (e.g., immediately adjacent) the inflection point than turns adjacent (e.g., immediately adjacent) the coronal and apical ends. The thread width of the at least one thread may be greater at turns adjacent (e.g., immediately adjacent) the coronal and apical ends than turns adjacent (e.g., immediately adjacent) the inflection point. The implant may have two threads extending around the core in a double-thread configuration.

The apical end may have a rounded shape and may extend beyond the at least one thread an extension distance (e.g., between 0.1 and 0.7 mm) in the apical direction.

The coronal region adjacent the coronal end may include one or more concave rings. At least a portion of the coronal region may have a frustoconical shape with decreasing size in a coronal direction.

The prosthetic interface is preferably configured for coupling to a prosthetic (e.g., crown, bridge, abutment). The prosthetic interface may include a Morse taper connection, internal threads, and/or an anti-rotation coupling in a polygon (e.g., hexagon) shape. The prosthetic interface may be adapted for direct coupling to a bridge or crown.

In accordance with another aspect, an implant for anchoring within bone (e.g., jawbone) is provided. The implant may include a coronal region having a coronal end and an apical region having an apical end, the apical end opposite the coronal end. The implant also may have a core, a prosthetic interface, and at least one thread. The core may extend from the coronal region to the apical region. The prosthetic interface is preferably at the coronal region (e.g., partially or fully). The at least one thread may extend around the core in a plurality of turns from the coronal region to the apical region and the at least one thread may have a plurality of curved notches that may each define a cutting edge. A first curved notch on a first turn need not substantially overlap with a second curved notch on a second turn, the second turn being adjacent the first turn in a coronal direction. The first curved notch need not substantially overlap with a third curved notch on a third turn, the third turn being adjacent the first turn in an apical direction. The overlap, if any, of the second and third curved notches with the first curved notch is preferably at opposing ends of the first curved notch.

The plurality of curved notches may each be partially notched to reflect a portion of a semi-spherical surface. The plurality of curved notches may each be partially notched to reflect a portion of a semi-cylindrical surface. The semi-spherical notch may intersect with the semi-cylindrical notch at each of the curved notches.

The second turn may be immediately adjacent the first turn in the coronal direction and the third turn may be immediately adjacent the first turn in the apical direction. In some embodiments, the first curved notch on the first turn does not overlap with the second curved notch on the second turn by more than 20% a width of the first curved notch (e.g., at one side of the first curved notch) and the first curved notch on the first turn does not overlap with the third curved notch on the third turn by more than 20% the width of the first curved notch (e.g., at an opposing side of the first curved notch). The first curved notch need not overlap with the second curved notch and need not overlap with the third curved notch.

In accordance with another aspect, an implant for anchoring within bone (e.g., jawbone) is provided. The implant may include a coronal region having a coronal end and an apical region having an apical end, the apical end opposite the coronal end. The implant also may have a core, a prosthetic interface, and at least one thread. The core may extend from the coronal region to the apical region. The prosthetic interface is preferably at the coronal region (e.g., partially or fully). The at least one thread may extend around the core in a plurality of turns from the coronal region to the apical region. The at least one thread may include a plurality of curved notches that may each define a cutting edge. In some embodiments, at least one of the plurality of curved notches is partially notched to reflect a portion of a semi-spherical surface and partially notched to reflect a portion of a semi-cylindrical surface. The semi-spherical notch may intersect with the semi-cylindrical notch.

Provided herein are methods of inserting the implants described above within bone. In accordance with one aspect, a method may include positioning an apical end of the implant at a desired location of the bone (e.g., at a predrilled bore hole in the jawbone where a prosthetic is to be placed to replace one or more teeth). The implant may have at least one thread extending around a core of the implant in a plurality of turns. The at least one thread may have a plurality of curved notches each defining a cutting edge where a partially semi-spherically curved portion of the notch meets the outer surface of the at least one thread. The method may further include rotating the implant (e.g., clockwise) such that the at least one thread cuts the bone contacted by the at least one thread to enlarge an opening in the bone as the implant is screwed into the bone. The at least one thread may have a self-drilling configuration (e.g., at least where the thread(s) begins at or adjacent the apical end of the implant) to compress bone as the implant is installed. During installation, the method may include applying a counter-torque by rotating the implant in the opposite direction (e.g., counterclockwise) to cut bone with at least one cutting edge. Such counter-torque rotation may be especially advantageous for removing dense/hard bone tissue encountered during installation. For example, the dentist/surgeon may apply the counter-torque to cut and remove the hard/dense bone material at a partial installation position before reaching the desired, full installation depth in the bone because, for example, the implant becomes stuck during installation. After counter-torque rotation, the method may include rotating the implant in the installation direction (e.g., clockwise) to complete installation. The method may also include repeating counter-torque rotation one or more additional times during installation at the same depth or a different depth(s) as the depth of the first counter-torque rotation. After installation, a prosthetic (e.g., crown, abutment, bridge) may be coupled to the implant directly or via an intermediate element such as an abutment.

In accordance with another aspect, a method may include positioning an apical end of the implant at a desired location of the bone (e.g., at a predrilled bore hole in the jawbone where a prosthetic is to be placed to replace one or more teeth). The implant may include at least one thread extending around a core of the implant in a plurality of turns. The at least one thread may have a thread outer diameter configured to define a cylindrical portion and a conical portion formed more apically than the cylindrical portion along a length of the implant. The method may further include rotating the implant such that the conical portion of the at least one thread increases an opening diameter in the bone as the conical portion enters the bone until the conical portion is fully screwed into the bone. The method also may include continuing to rotate the implant such that the cylindrical portion of the at least one thread enters the bone without increasing the opening diameter in the bone. The cylindrical portion outer diameter may be equal to the maximum outer diameter of the conical portion. In addition, the cylindrical portion may be formed along at least 25% of the length of the thread.

V. BRIEF DESCRIPTION OF THE DRAWINGS

Figure 1A:
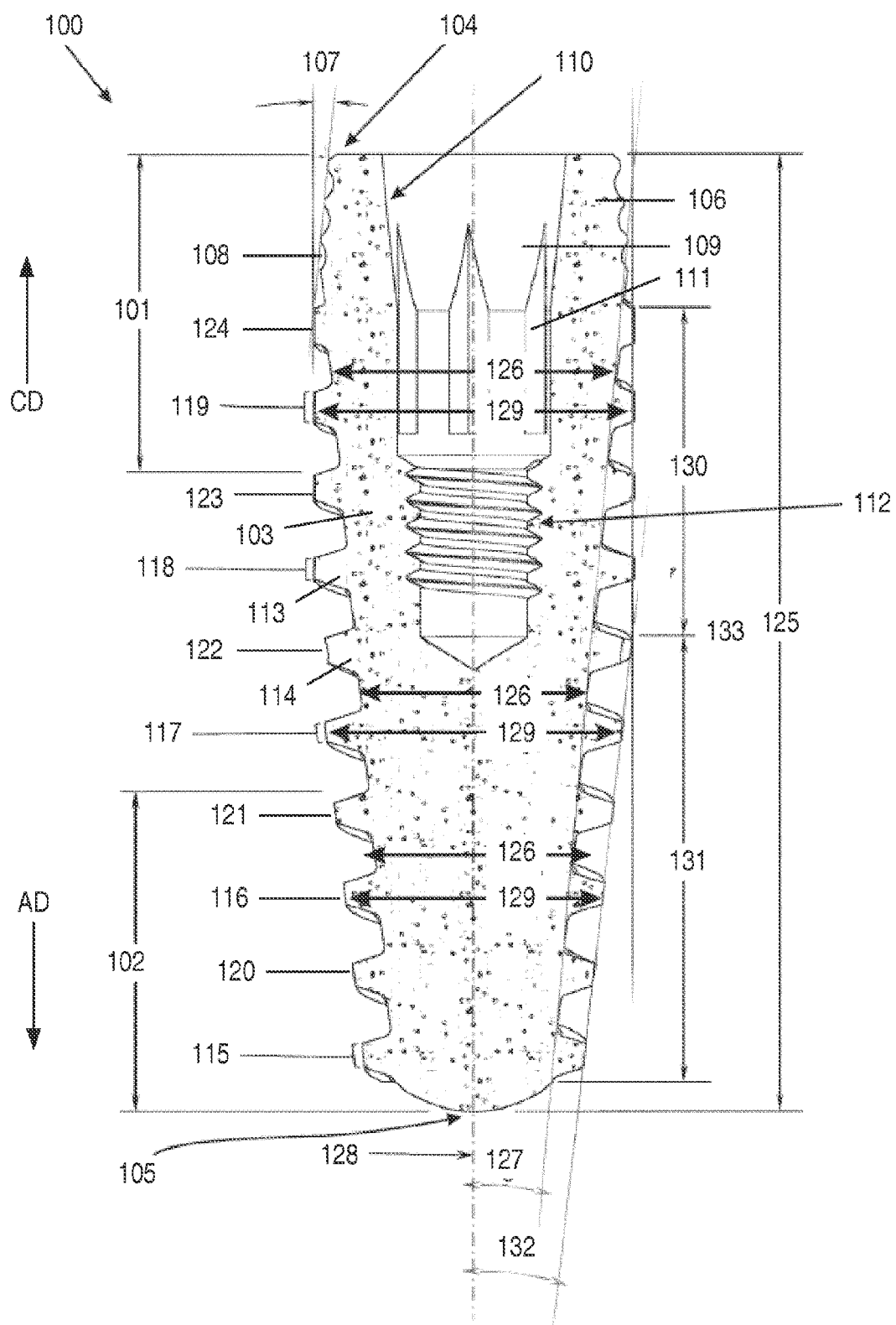
FIG. 1A shows a cross-sectional view of an embodiment of an exemplary implant constructed in accordance with the principles of the present disclosure.

FIGS. 1G, 1H, and 1I show top, isometric, and side views, respectively, of the implant of FIG. 1A.

Figure 2A:
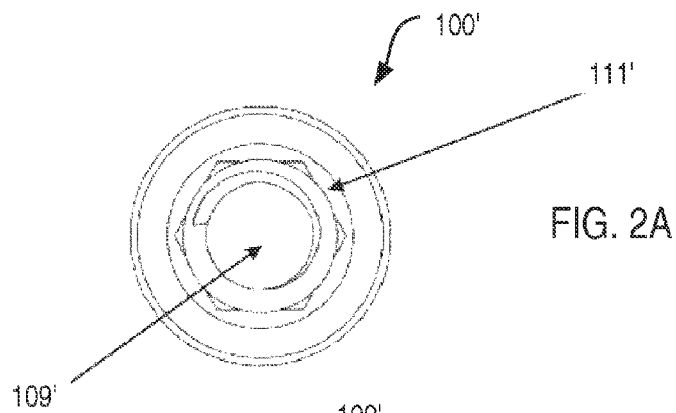
Figure 2B:
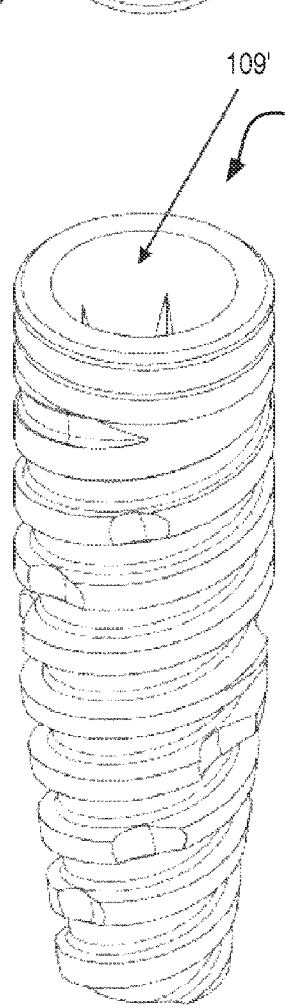
Figure 2C:
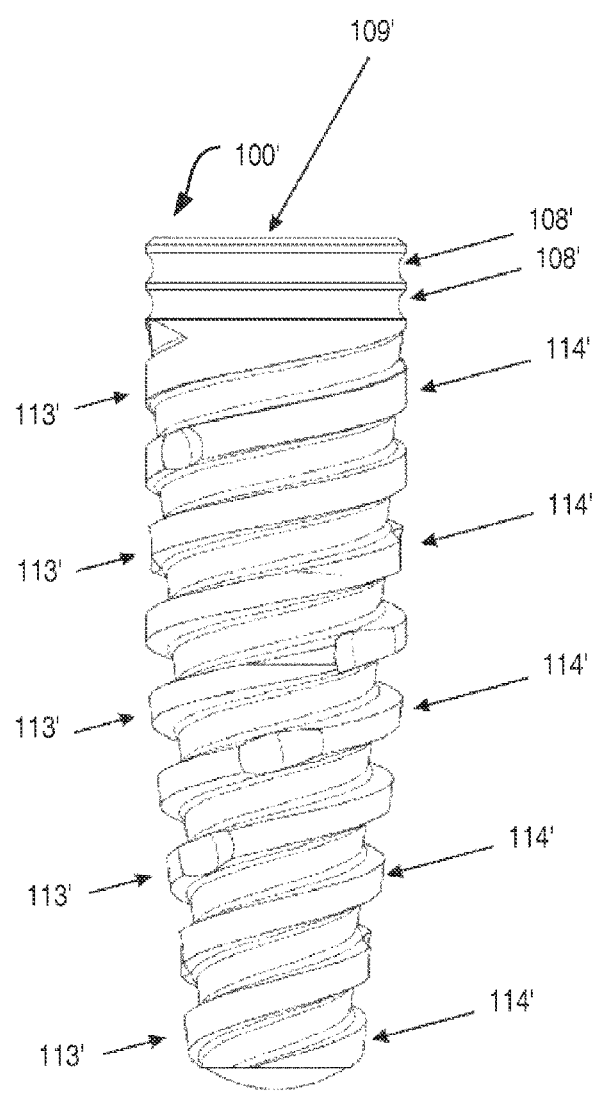

FIGS. 2A, 2B, and 2C show top, isometric, and side views, respectively, of an alternative embodiment of an exemplary implant constructed in accordance with the principles of the present disclosure.

FIGS. 3A, 3B, and 3C show top, isometric, and side views, respectively, of an another embodiment of an exemplary implant constructed in accordance with the principles of the present disclosure, including a prosthetic interface in the form of an external hexagon.

FIGS. 4A, 4B, and 4C show top, isometric, and side views, respectively, of an yet another embodiment of an exemplary implant constructed in accordance with the principles of the present disclosure, wherein a part of the prosthetic geometry is integral with the implant in a one-piece implant manner.

VI. DETAILED DESCRIPTION OF THE INVENTION

Osseointegrated implants are provided herein that may be used to anchor prosthetic structures, bone substitutes, and/or corrective elements on the human skeleton. The implants may be dental Osseointegrated implants in the form of screws designed to be anchored to the jawbone via the mouth to support prosthetic substitutes for one or more missing, lost, removed, and/or damaged teeth.

Referring now to FIG. 1A, a cross-sectional view of an exemplary implant constructed in accordance with the principles of the present disclosure is provided. Implant 100 is adapted for anchoring within bone. In a preferred embodiment, implant 100 is a dental Osseointegrated implant adapted for anchoring within the jawbone via the mouth to support prosthetic substitutes for one or more missing, lost, removed, and/or damaged teeth.

Implant 100 may include coronal region 101, apical region 102, and core 103 extending from coronal region 101 to apical region 102. Coronal region 101 is at the upper portion of implant 100 and includes coronal end 104 at the upper most end, while apical region 102 is at the lower portion of implant and includes apical end 105 at the lower most end, opposite coronal end 104. Apical region 102 is adapted for insertion into bone prior to coronal region 101. Apical end 105 may be first inserted into the bone and implant 100 then is screwed down to the proper depth using, for example, drilling tools adapted to engage a portion of implant 100 at coronal region 101. Apical end 105 may be flat, but preferably has a rounded shape to minimize damage to the Sinus membrane if implant 100 is advanced excessively during installation. Further, in order to prevent damages, apical end 105 extends in an apical direction AD an amount beyond the beginning of the implants thread(s), e.g., between 0.1 and 0.7 mm, between 0.25 and 0.5 mm.

Implant 100 may be screwed such that coronal end 104 of coronal region 101 is beneath, flush with, or above the outer bone surface, and preferably coronal end 104 remains exposed for subsequent installation of the component(s) (e.g., abutment, crown, bridge) that will be anchored on implant. Coronal region 101 of implant 100 may include frustoconical portion 106 tapering in the coronal direction CD such that the outer diameter at frustoconical portion 106 decreases in the coronal direction CD at frustoconical angle 107 (e.g., between 1 and 60°, between 1 and 45°, between 1 and 30°, between 5 and 30°, between 5 and 25°, between 5 and) 20°. Frustoconical portion 107 may begin where the implant thread(s) end and continue in the coronal direction CD to coronal end 104. Alternatively, coronal region 101 need not include frustoconical portion 107 and the implant thread(s) may end at coronal end 104 or there may be a portion of coronal region 101 extending beyond the end of the thread(s) that has a constant diameter or a shape other than frustoconical.

Coronal region 101 of implant 100 may include one or more channels arranged in the form of one or more concave rings 108. Concave rings 108 may at frustoconical portion 107 and, illustratively, there are three concave rings 108. Concave rings 108 may have a ratio between the radius of the concave ring and the depth of concavity of the concave ring being of about 2:1, 3:1, 4:1, 5:1, or 6:1.

Implant 100 also may include prosthetic interface 109 at coronal region 101. Prosthetic interface 109 is configured to couple to a prosthetic (e.g., abutment, crown, bridge) directly or via another component, such as an abutment. Prosthetic interface 109 may be within implant 100 and engaged through coronal end 104, as illustrated in FIG. 1A, or may be partially or fully exposed, for example, in a one-piece configuration, as discussed below. Prosthetic interface 109 may take any form suitable for engaging a prosthetic such as, for example, conical, hexagonal, and octagonal, used in conjunction or separately. Prosthetic interface 109 is also configured to minimize relative movement, in particular rotation motion, between implant 100 and the prosthetic coupled thereto.

In FIG. 1A, prosthetic interface 109 includes Morse Taper connection 110 associated with internal polygon 111 (illustratively a hexagon) for engaging the prosthetic. Prosthetic interface 109 may also include internal threads 112 to fix to corresponding threads in the prosthetic. Prosthetic interface 109 may be temporarily coupled to an installation tool, such as a transfer piece, screw driver, and/or drill, for installing implant 100 within bone.

Implant 100 preferably includes at least one thread extending around core 103 in a plurality of turns from coronal region 101 to apical region 102. As is clear in FIG. 1A, the thread(s) may extend from coronal region 101 to apical region 102 even though the entire coronal region 101 and/or the entire apical region 102 need not be threaded. The thread(s) is preferably self-drilling and need not include a self-tapping structure such as a bone tap. In a self-drilling design, implant 100 is configured to drill itself into biological material, although a predrilled bore hole may be used to assist with starting insertion of implant 100 into the biological material. In addition, as explained below, the thread(s) may have one or more notches to remove bone (e.g., dense/hard bone) during installation (e.g., by counter-torquing).

Illustratively, implant 100 has first thread 113 and second thread 114 each extending around core 103 in a plurality of turns from coronal region 101 to apical region 102. First thread 113 and second thread 114 are counterposed to form a double-thread configuration such that one 360° rotation of implant 100 causes two ridges of implant 100 to be inserted (e.g., past one turn from first thread 113 and one turn from second thread 114). First thread 113 has turns 115, 116, 117, 118, and 119 each formed by a 360° rotation of first thread 113 around core 103. Second thread 114 has turns 120, 121, 122, 123, and 124 each formed by a 360° rotation of second thread 114 around core 103. As will be readily apparent to one skilled in the art, the number of thread(s) on implant 100 may be selected based on the desired number of rotations required to install implant 100. While implant 100 illustratively has first thread 113 and second thread 114, the implants provided herein could have a single thread, a triple thread, a quadruple thread, etc.

Implant 100 has length 125 and preferably has diameters that vary throughout length 125 configured to reduce removal of biological material (e.g., bone, blood vessels within the bone) as compared to a conventional implant. Length 125 is selected according to the biological space available for insertion. For example, length 125 may be a suitable length for insertion in the jawbone.

Preferably, the thread(s) of the implant has an outer diameter(s) that increases in the coronal direction CD from the beginning of the thread(s) at or near apical end 105 and then the thread(s) outer diameter(s) is constant for a portion of the implant (e.g., at least 20% of length 125 of implant 100, at least 25% of length 125 of implant 100, at least 30% of length 125 of implant 100, at least 35% of length 125 of implant 100, at least 40% of length 125 of implant 100, at least 45% of length 125 of implant 100, at least 50% of length 125 of implant 100, at least 55% of length 125 of implant 100, at least 60% of length 125 of implant 100) to reduce removal of biological material. In at least one embodiment, the outer diameter(s) of the thread(s) becomes constant at about the midpoint of length 125 of implant 100. As compared to a conventional implant, which generally has an increasing outer diameter of the thread(s) in the coronal direction throughout the length of the threads, the thread(s) described herein are configured to reduce the removal of biological material (e.g., bone, blood vessels within the bone) during implant installation by increasing the opening diameter within the bone for only a portion (e.g., a conical portion) of the threaded area of the implant, thereby decreasing the amount of biologic material removed during the installation, providing increased stability, and reducing healing time.

As shown in FIG. 1A, core 103 has core outer diameter 126 that may decrease at core diameter decrease rate 127 in the apical direction AD towards apical end 105. For example, core outer diameter 126 may be greatest in coronal region 101 and smallest in apical region 102. In one embodiment, core outer diameter 126 is greatest at the most apical end of frustoconical portion 106 and smallest at or adjacent to apical end 105. Core diameter decrease rate 127 may decrease at an angle relative to longitudinal axis 128. The angle is preferably acute and may be between 1 and 60°, between 1 and 45°, between 1 and 30°, between 5 and 30°, between 5 and 25°, between 5 and 20°, between 1 and 20°, between 1 and 15°, between 15 and 15°. The angle may be constant such that core diameter decrease rate 127 remains constant from coronal region 101 to apical region 102.

The thread(s) of implant 100 has thread outer diameter 129 that may be configured to define cylindrical portion 130 and conical portion 131. Cylindrical portion 130 is more in the coronal direction CD than conical portion 131 along implant 100. In cylindrical portion 130, thread outer diameter 129 preferably remains constant for more than one turn around core 103. Cylindrical portion 130 may be positioned at least partially in coronal region 101. Thread outer diameter 129 in cylindrical portion 130 may be equal to thread outer diameter 129 at the most coronal part of conical portion 131. In conical portion 131, thread outer diameter 129 preferably decreases at thread diameter decrease rate 132 in the apical direction AD. Conical portion 131 may be positioned at least partially in apical region 102. Thread diameter decrease rate 132 may decrease at a lesser rate, the same rate, or at a greater rate than core diameter decrease rate 127. As illustrated, thread diameter decrease rate 132 decreases at a greater rate than core diameter decrease rate 127. Thread diameter decrease rate 132 may decrease at an angle relative to longitudinal axis 128. The angle is preferably acute and may be between 1 and 60°, between 1 and 45°, between 1 and 30°, between 5 and 30°, between 5 and 25°, between 5 and 20°, between 1 and 20°, between 1 and 15°, between 15 and 15°. The angle may be constant such that thread diameter decrease rate 132 remains constant in conical portion 131. As illustrated, thread diameter decrease rate 132 is greater than core diameter decrease rate 127 throughout the entire conical portion 131.

Cylindrical portion 130 and conical portion 131 may meet at inflection point 133 where thread outer diameter 129 transitions from constant to decreasing towards apical end 105. Inflection point 133 may be at the midway point along length 125 of implant 100 or within 10%, 20%, or 30% of the midway point of implant. On implant 100, the ratio of the length of conical portion 131 to length 125 of implant 100 may range from 1:3 to 2:3, and preferably is 1:2.

The difference between core outer diameter 126 and thread outer diameter 129 may be greatest at inflection point 133 and the difference between diameters 126, 129 may decrease in the coronal direction CD (e.g., from inflection point 133) in cylindrical portion 130 (e.g., throughout the entire cylindrical portion 130). For example, in cylindrical portion 130, the difference between core outer diameter 126 and thread outer diameter 129 may be greatest at the most apical point of cylindrical portion 130 and smallest at the most coronal point of cylindrical portion 130. The difference between core outer diameter 126 and thread outer diameter 129 may decrease in the apical direction AD (e.g., from inflection point 133) in conical portion 131 (e.g., throughout the entire conical portion 131). For example, in conical portion 131, the difference between core outer diameter 126 and thread outer diameter 129 may be greatest at the most coronal point of conical portion 131 and smallest at the most apical point of conical portion 131. The difference between core outer diameter 126 and thread outer diameter 129 may be proportional at the turn closest to coronal end 104 to the difference between core outer diameter 126 and thread outer diameter 129 at the turn closest to apical end 105.

In FIG. 1A, cylindrical portion 130 includes turns 118 and 119 of first thread 113 and turns 123 and 124 of second thread 114 while conical portion 131 includes turns 115, 116, and 117 of first thread 113 and turns 120, 121, and 122 of second thread 114.

Figure 1B:
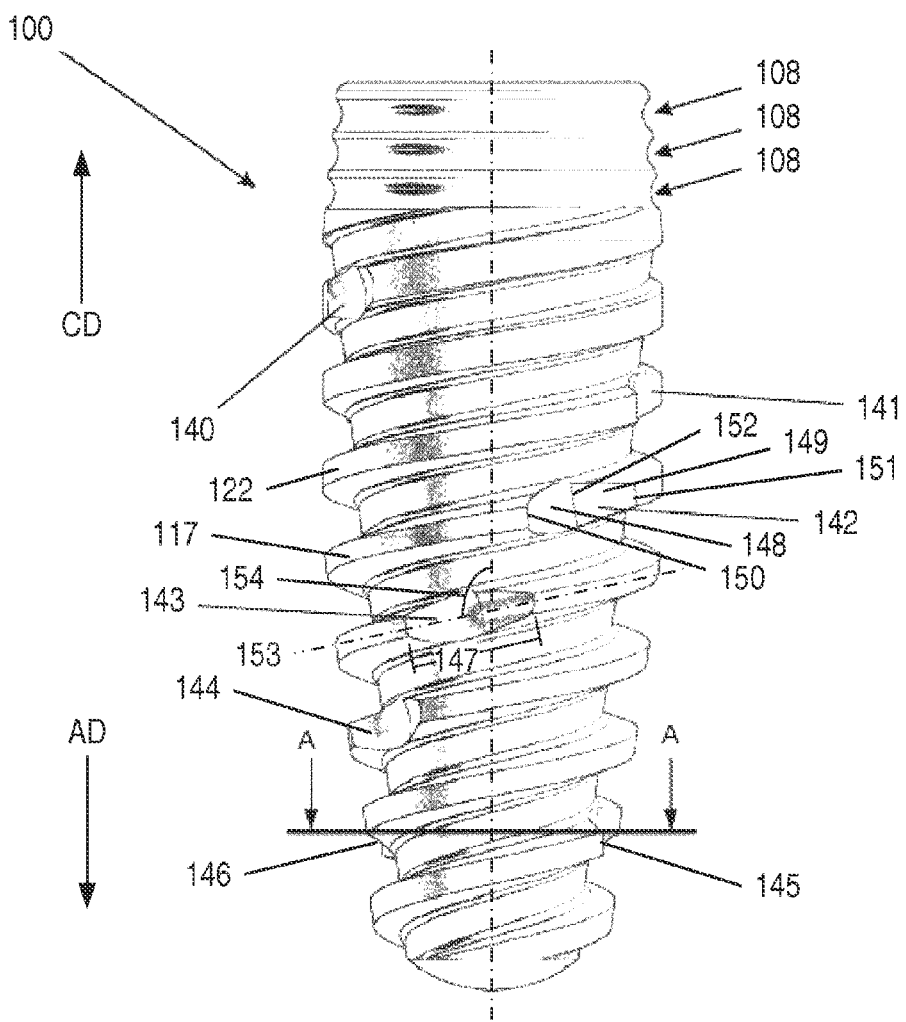
FIG. 1B illustrates a side view of the implant shown in FIG. 1A.
Figure 1C:
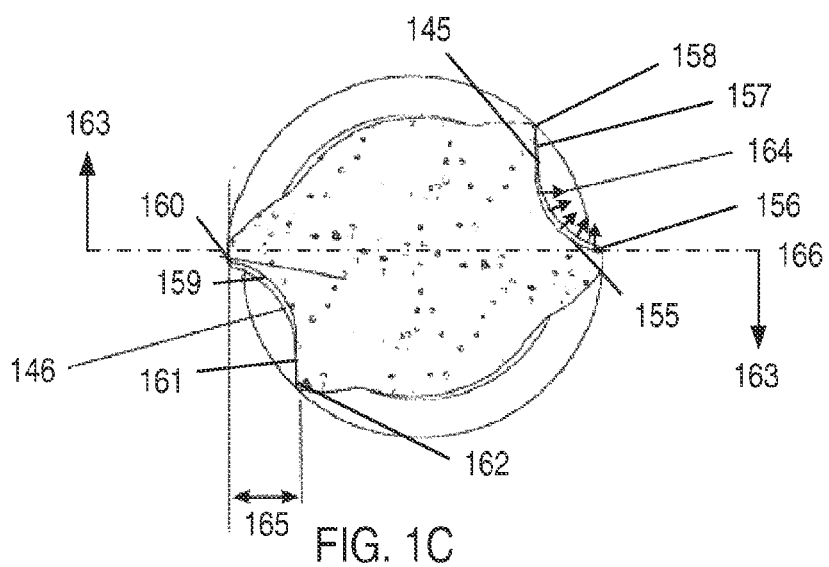
FIG. 1C shows a cross-sectional view of the implant along line AA in FIG. 1B, including details of the notches.

Referring now to FIGS. 1B and 1C, additional details on the thread(s) and notches within the thread(s) are shown. Preferably, the thread(s) have a plurality of notches spaced radially and longitudinally from one another along the implant. As compared to a conventional bone tap, which is a continuous cut through a plurality of turns of the thread(s), the notches described herein are configured to permit selective removal of bone (e.g., dense/hard bone) during implant installation. For example, the notches may be used to cut bone (including dense/hard bone) through application of counter-torque force to the bone. A dentist/surgeon may rotate the implant in a direction opposite the installation direction such that one or more notches cuts through the bone at a partial installation position (e.g., when dense/hard bone is encountered) to permit further installation.

One or more of the curved notches may be partially notched to reflect a portion of a semi-spherical surface and/or may be partially notched to reflect a portion of a semi-cylindrical surface. The semi-spherical surface may intersect the semi-cylindrical surface at each notch. One or more of the curved notches may define a cutting edge at the respective notch, e.g., where the semi-spherical surface of the notch meets the thread outer diameter surface. One or more of the curved notches also may define an opposing edge, opposite the cutting edge, at the respective notch, e.g., where the semi-cylindrical surface of the notch meets the thread outer diameter surface. In a preferred embodiment, each curved notch of the implant defines a cutting edge, where a partially semi-spherically curved portion of the notch meets the outer surface of the thread, and an opposing edge, where a partially semi-cylindrically curved portion of the notch meets the outer surface of the thread.

In FIG. 1B, curved notches 140, 141, 142, 143, 144, 145, and 146 are notched into the thread(s) over a plurality of turns. Curved notches 140, 141, 142, 143, 144, 145, and 146 are spaced apart from one another radially and longitudinally along the length of the thread(s). As shown, curved notch 141 is notched into turn 122 of second thread 114, curved notch 142 is notched into turn 117 of first thread 113, and curved notch 143 is notched into turn 121 of second thread 114. Unlike a conventional bone tap, the curved notches need not substantially overlap with one another in the coronal direction CD and/or the apical direction AD. For example, curved notch 142 does not substantially overlap with curved notch 141, which is on a turn adjacent in the coronal direction CD (illustratively, immediately adjacent), and curved notch 142 does not substantially overlap with cured notch 143, which is on a turn adjacent in the apical direction AD (illustratively, immediately adjacent). "Does not substantially overlap" as described herein means that the notches do not overlap: by more than 50% the width 147 of the notch, by more than 40% the width 147 of the notch, by more than 30% the width 147 of the notch, by more than 25% the width 147 of the notch, by more than 20% the width 147 of the notch, by more than 15% the width 147 of the notch, by more than 10% the width 147 of the notch, by more than 5% the width 147 of the notch, and/or do not overlap. For example, if a notch has a width of 10 mm and the notch does not substantially overlap another notch by more than 10% the width, than at most 1 mm of the 10 mm width can overlap with the adjacent notch in the coronal direction CD or the apical direction AD. That notch could also overlap by, at most, 1 mm with the adjacent notch in the other direction (coronal or apical). A curved notch may overlap minimally at its cutting edge side with an adjacent notch at its opposing edge side and the curved notch may overlap minimally at its opposing edge side with a different adjacent notch at its cutting edge side.

Referring still to FIG. 1B, curved notch 142 is shown as having semi-spherical face 148, where curved notch 142 is partially notched to reflect a portion of a semi-spherical surface, and semi-cylindrical face 149, where curved notch 142 is partially notched to reflect a portion of a semi-cylindrical surface. The semi-spherical face may intersect the semi-cylindrical face at each notch. Curved notch 142 defines cutting edge 150 where semi-spherical face 148 meets the thread outer diameter surface. Cutting edge 150 is positioned on the thread such that cutting edge 150 contacts biological material (e.g., bone, blood vessels with the bone) before other portions of the notch. Cutting edge 150 is configured to cut through the biological material (e.g., preferably including dense/hard bone) during installation when counter-torque action is applied to the implant (e.g., screwing in the counterclockwise direction opposite the installation direction). Cutting edge 150 may also cut through biological material during removal or adjustment of implant 100, e.g., during unscrewing in the counterclockwise direction, by cutting through biological material. Curved notch 142 also defines opposing edge 151, opposite cutting edge 150 of notch 142, where semi-cylindrical face 149 meets the thread outer diameter surface.

Use of a curved notch(es) with a semi-spherical face and a semi-cylindrical face enhances cutting during counter-torquing, adjustment, and/or removal of the implant and enhances integrity of the threads. Semi-spherical face 148 may intersect with semi-cylindrical face 149 at intersection point 152 of curved notch 142. Intersection point 152 may be at the midway point of the width of the notch. The semi-spherical face of the notch(es) may be notched into the thread(s) with a spherical end of an machining tool to mill the surface to reflect a portion of a semi-spherical surface.

The curved notch(es) may be inclined relative to longitudinal axis 128 of implant 100. In FIG. 1B, centerline 153 runs through the center of curved notch 143 and is inclined at the angle of the thread. Curved notch 143 is inclined between centerline 153 and longitudinal axis 128 at notch inclination angle 154 (e.g., between 65 and 135°, between 65 and 115°, between 90 and 135°, between 90 and 115°, between 100 and 125°, between 100 and 115°).

The curved notch(es) may be radially distributed from adjacent notches (e.g., on the same thread or a different thread) at distribution angles, using longitudinal axis 128 as a central pivot point. For example, a curved notch may be distributed at a distribution angle (e.g., between 30 and 180°, between 60 and 180°, between 30 and 120°, between 60 and 120°, between 90 and 180°) from its adjacent notch (e.g., immediately adjacent) in the coronal and/or apical direction.

In addition, the curved notch(es) may be angled relative to adjacent notches (e.g., on the same thread or a different thread) at notch angles, using longitudinal axis 128 as a central pivot point. For example, a curved notch may be angled at a notch angle (e.g., between 10 and 80°, between 20 and 60°, between 30 and 60°, between 35 and 55°, 45°) from its adjacent notch (e.g., immediately adjacent) in the coronal and/or apical direction.

Referring now to FIG. 1C, a cross-sectional view of implant 100 along line AA in FIG. 1B is shown. Curved notch 145 has semi-spherical face 155 defining cutting edge 156 and semi-cylindrical face 157 defining opposing edge 158. Curved notch 146 has semi-spherical face 159 defining cutting edge 160 and semi-cylindrical face 161 defining opposing edge 162. To facilitate cutting during counter-torquing, adjustment, and/or removal, the semi-spherical face(s) of the notch(es) may have a portion of the normal vectors pointing with a deviation angle in the opposite direction of implant installation direction 163. As shown at curved notch 145, semi-spherical face 155 has a portion (e.g., at least 5%, at least 10%, at least 20%, at least 30%, at least 40%, at least 50%) of normal vectors 164 pointing with a deviation angle (e.g., between 1 and 15°, between 1 and 10°, between 5 and 15°, between 5 and 15°, up to 15°) the opposite direction of implant installation direction 163. Cutting edge 156 may cut biological material in an opposite direction related to the direction of installation 163 due to a concentration of normal vectors 164 at semi-spherical face 155 near and on cutting edge 156, as seen in FIG. 1C. As shown at curved notch 146, semi-cylindrical face 161 may be in the form of a substantially straight line 165 parallel to the tangent line of the outer face of the thread, wherein the tangent line matches cutting edge 160. Semi-cylindrical face 161 may be perpendicular to where cutting edge 160 meets the outer thread surface at center axis 166.

Figure 1D:
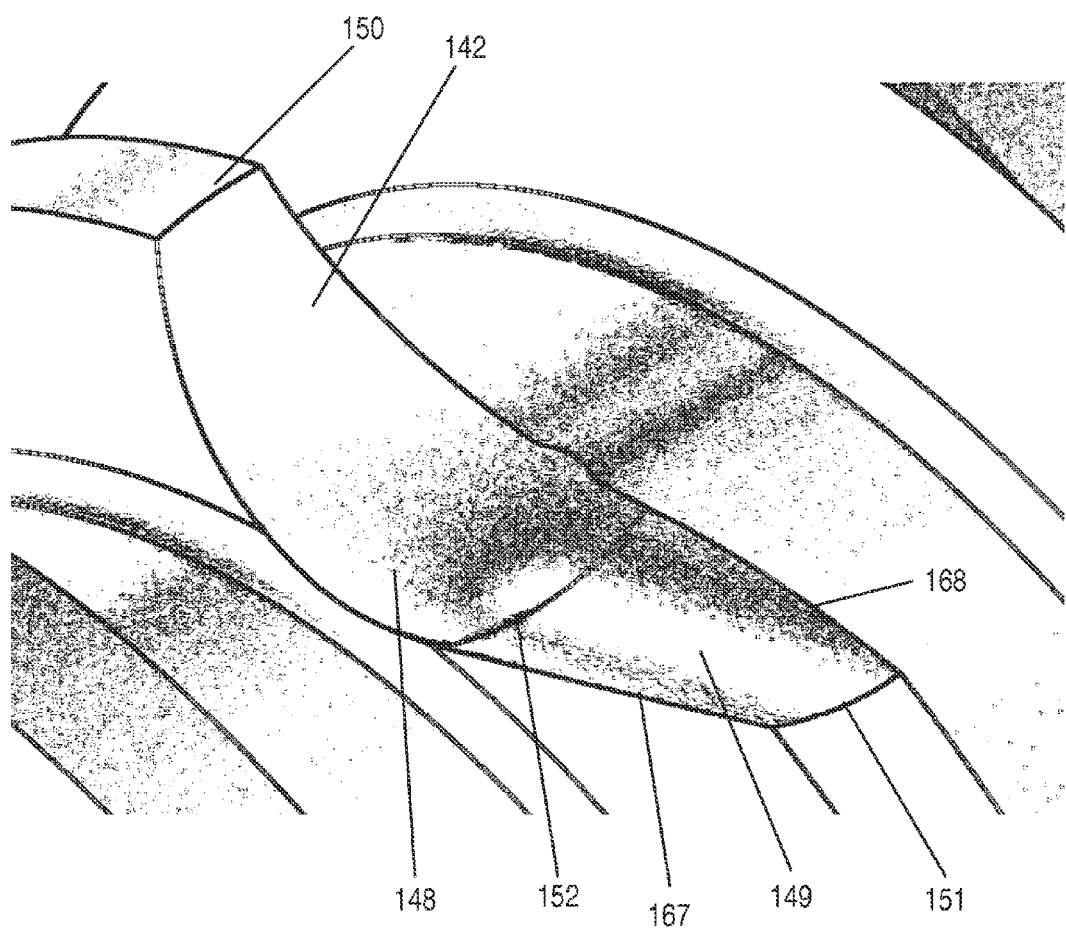
FIG. 1D illustrates a close-up view of a curved notch for use in the implant of FIG. 1A.

FIG. 1D shows a close-up view of a curved notch (illustratively curved notch 142) that may be incorporated in the thread(s) of the implants described herein. A curved notch may have two curved faces of differing geometries that may intersect at the deepest point of the curve and define cutting and opposing edges at the outer ends of the notch. As described above, the differing geometries may be a semi-spherical face that reflects a portion of a surface of a semi-sphere and a semi-cylindrical face that reflects a portion of a surface of a semi-cylinder. In FIG. 1D, curved notch 142 includes semi-spherical face 148 that defines cutting edge 150 and semi-cylindrical face 149 that defines opposing edge 151. Semi-spherical face 148 and semi-cylindrical face 149 meet at intersection point 152. Semi-cylindrical face 149 may reflect a portion of semi-cylindrical surface where the semi-cylinder is laying lengthwise such that apical edge 167 and coronal edge 168 of curved notch 142 are straight at semi-cylindrical face 149. Semi-cylindrical face 149 may curve inward from apical edge 167 and from coronal edge 168 to reflect a portion of a semi-cylindrical surface. In semi-spherical face 148, apical edge 167 and coronal edge 168 are curved to reflect a portion of a semi-spherical surface. Semi-spherical face 148 may curve inward from apical edge 167 and from coronal edge 168 to reflect a portion of a semi-spherical surface.

Figure 1E:
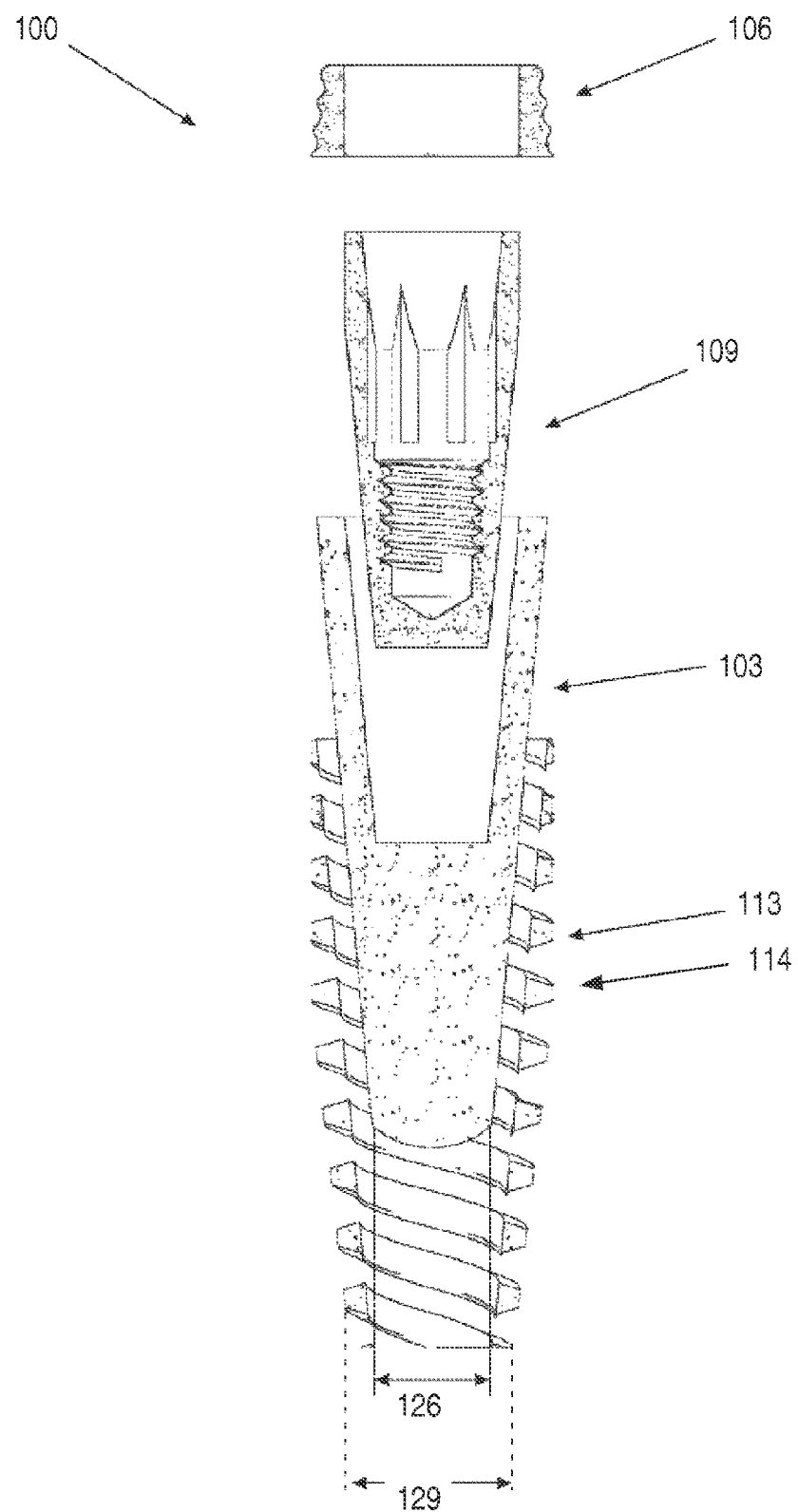
FIG. 1E illustrates a frustoconical portion, a prosthetic interface portion, a core portion, and threads of the implant of FIG. 1A separated from one another for illustrative purposes.

Referring now to FIG. 1E, core 103, frustoconical portion 106, prosthetic interface 109, and first and second threads 113, 114 of implant 100 are shown separated from one another for illustrative purposes. Core outer diameter 126 and thread outer diameter 129 are shown at parts adjacent the apical end of implant 100.

Figure 1F:
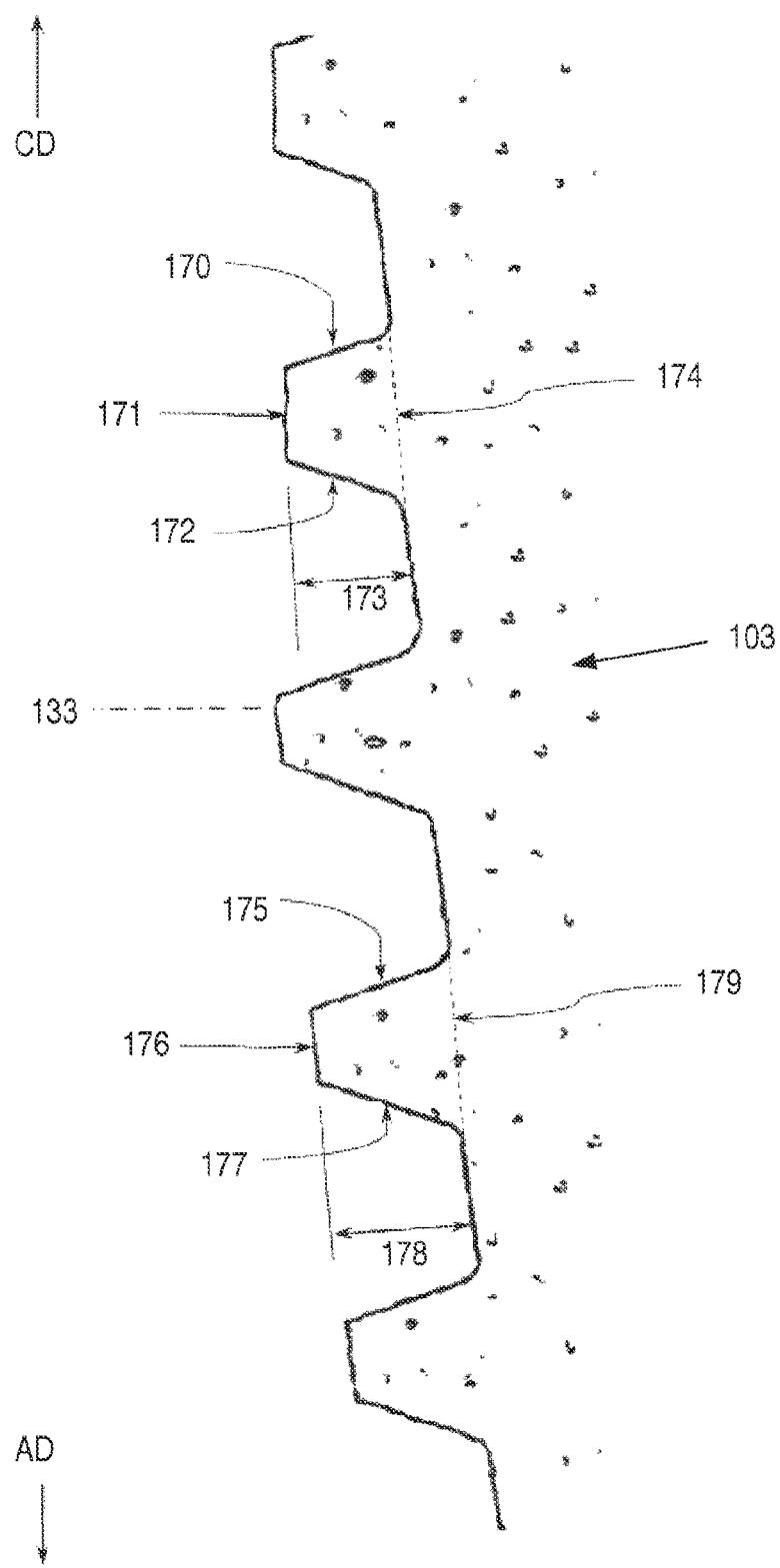
FIG. 1F shows details of the thread design of the implant of FIG. 1A.

Referring to FIG. 1F, a thread design that may be used in implant 100 is shown. Each cross section of the thread has a coronal face, an outer face, an apical face, and a height. For example, the thread at the turn immediately adjacent inflection point 133 in the coronal direction CD has coronal face 170, outer face 171, apical face 172, height 173, and base width 174. Height 173 is the distance between core 103 and outer face 171 at that turn. Base width 174 is the distance between coronal face 170 and apical face 172 where the faces meet core 103. Thread width is the distance between coronal face 170 and apical face 172 at outer face 171. As another example, the thread at the turn immediately adjacent inflection point 133 in the apical direction AD has coronal face 175, outer face 176, apical face 177, height 178, and base width 179. Height 178 is the distance between core 103 and outer face 176 at that turn. Base width 179 is the distance between coronal face 175 and apical face 177 where the faces meet core 103. Thread width is the distance between coronal face 175 and apical face 177 at outer face 176.

Implant 100 may have variable thread heights and/or variable thread widths. For example, the thread height may be greater at turns adjacent inflection point 133 than turns adjacent the coronal and apical ends. The thread width may be greater at turns adjacent the coronal and apical ends than turns adjacent inflection point 133.

FIGS. 1G, 1H, and 1I show top, isometric, and side views, respectively, of implant 100. In FIGS. 1G, 1H, and 1I, prosthetic interface 109 includes a Morse Taper connection associated with internal polygon 111 (illustratively a hexagon) for engaging the prosthetic. For implant 100, the length may be considered as from the apical end to the coronal end including the back taper.

Referring now to FIGS. 2A, 2B, and 2C, implant 100' is constructed similarly to implant 100 of FIGS. 1A to 1I, wherein like components are defined by like-primed reference numbers. Thus, for example, first thread 113 of FIGS. 1A to 1I corresponds to first thread 113' of FIGS. 2A, 2B, and 2C. As will be observed by comparing FIGS. 1G, 1H, and 1I to FIGS. 2A, 2B, and 2C, implant 100' has two concave rings 108' instead of three concave rings in the coronal region.

Referring now to FIGS. 3A, 3B, and 3C, implant 100" is constructed similarly to implant 100 of FIGS. 1A to 1I, although implant 100" has a modified prosthetic interface. Implant 100" has prosthetic interface 300 with external polygon 301 (illustratively a hexagon) for engaging the prosthetic, rather than an internal polygon. For implant 100", the length may be considered as from the apical end to the coronal end of the implant, including the external polygon.

Referring now to FIGS. 4A, 4B, and 4C, implant 100''' is constructed similarly to implant 100 of FIGS. 1A to 1I, although implant 100''' has a modified prosthetic interface. Implant 100''' has prosthetic interface 400 for engaging the prosthetic in a one-piece type configuration. Prosthetic interface 400 is adapted to directly couple to the prosthetic crown or bridge, without the need for an intermediate element (e.g., an abutment) and thus preventing coupling between two parts in the sub-gums region. Prosthetic interface 400 may be shaped as a cylinder 401, whose outer diameter may vary although the maximum outer diameter of cylinder 401 is preferably less than or equal to the maximum thread outer diameter of the implant. For implant 100''', the length may be considered as from the apical end to the coronal end of the concave rings. As will be observed by comparing FIGS. 4B and 4C, implant 100''' may or may not include concave rings 108'''. When implant 100''' does not include concave rings 108''', the length may be considered as from the apical end to the end of the threads.

The implants provided herein may be made from a biocompatible metal(s), such as titanium and alloys thereof, and may be coated with other types of biocompatible materials, such as hydroxyapatite, and/or receive a surface treatment in order to improve the osseointegration quality of the implant surface(s).

Provided herein are methods of inserting the implants described above within bone. In accordance with one aspect, a method may include positioning an apical end of the implant at a desired location of the bone (e.g., at a predrilled bore hole in the jawbone where a prosthetic is to be placed to replace one or more teeth). The implant may have at least one thread extending around a core of the implant in a plurality of turns. The at least one thread may have a plurality of curved notches each defining a cutting edge where a partially semi-spherically curved portion of the notch meets the outer surface of the at least one thread. The method may further include rotating the implant (e.g., clockwise) such that the at least one thread cuts the bone contacted by the at least one thread to enlarge an opening in the bone as the implant is screwed into the bone. The at least one thread may have a self-drilling configuration (e.g., where the thread(s) begins at or adjacent the apical end of the implant) to compress bone as the implant is installed. During installation, the method may include applying a counter-torque by rotating the implant in the opposite direction (e.g., counter-clockwise) to cut bone with at least one cutting edge. Such counter-torque rotation may be especially advantageous for removing dense/hard bone tissue encountered during installation. For example, the dentist/surgeon may apply the counter-torque to cut and remove the hard/dense bone material at a partial installation position before reaching the desired, full installation depth in the bone because, for example, the implant becomes stuck during installation. After counter-torque rotation, the method may include rotating the implant in the installation direction (e.g., clockwise) to complete installation. The method may also include repeating counter-torque rotation during installation at the same depth or a different depth(s) as the depth of the first counter-torque rotation. After installation, a prosthetic (e.g., crown, abutment, bridge) may be coupled to the implant directly or via an intermediate element such as an abutment.

In accordance with another aspect, a method may include positioning an apical end of the implant at a desired location of the bone (e.g., at a predrilled bore hole in the jawbone where a prosthetic is to be placed to replace one or more teeth). The implant may include at least one thread extending around a core of the implant in a plurality of turns. The at least one thread may have a thread outer diameter configured to define a cylindrical portion and a conical portion formed more apically than the cylindrical portion along a length of the implant. The method may further include rotating the implant such that the conical portion of the at least one thread increases an opening diameter in the bone as the conical portion enters the bone until the conical portion is fully screwed into the bone. The method also may include continuing to rotate the implant such that the cylindrical portion of the at least one thread enters the bone without increasing the opening diameter in the bone. The cylindrical portion outer diameter may be equal to the maximum outer diameter of the conical portion. In addition, the cylindrical portion may be formed along at least, for example, 25% of the length of the thread.

Definitions

Unless otherwise defined, each technical or scientific term used herein has the same meaning as commonly understood by one of ordinary skill in the art to which this disclosure belongs. In accordance with the claims that follow and the disclosure provided herein, the following terms are defined with the following meanings, unless explicitly stated otherwise.

The term "about" or "approximately," when used before a numerical designation or range (e.g., pressure or dimensions), indicates approximations which may vary by (+) or (−) 5%, 1% or 0.1%.

As used in the specification and claims, the singular form "a", "an" and "the" include both singular and plural references unless the context clearly dictates otherwise. For example, the term "a thread" may include, and is contemplated to include, a plurality of threads. At times, the claims and disclosure may include terms such as "a plurality," "one or more," or "at least one;" however, the absence of such terms is not intended to mean, and should not be interpreted to mean, that a plurality is not conceived.

As used in the specification and claims, "at least one of" means including, but not limited to, one or more of any combination of the following. For example, "at least one of A, B, and C" means including, but not limited to, A(s) or B(s) or C(s) or A(s) and B(s) or A(s) and C(s) or B(s) and C(s) or A(s) and B(s) and C(s); none of which excludes other elements such as D(s), E(s), etc.

As used herein, the term "comprising" or "comprises" is intended to mean that the devices, systems, and methods include the recited elements, and may additionally include any other elements. "Consisting essentially of" shall mean that the devices, systems, and methods include the recited elements and exclude other elements of essential significance to the combination for the stated purpose. Thus, a device or method consisting essentially of the elements as defined herein would not exclude other materials or steps that do not materially affect the basic and novel characteristic(s) of the claimed invention. "Consisting of" shall mean that the devices, systems, and methods include the recited elements and exclude anything more than a trivial or inconsequential element or step. Embodiments defined by each of these transitional terms are within the scope of this disclosure.

While various illustrative embodiments of the invention are described above, it will be apparent to one skilled in the art that various changes and modifications may be made therein without departing from the invention. The appended claims are intended to cover all such changes and modifications that fall within the true scope of the apparatus and methods of the present invention.

What is claimed:

1. An implant for anchoring within bone, the implant comprising:
   a coronal region comprising a coronal end;
   an apical region comprising an apical end, the apical end opposite the coronal end;
   a core extending from the coronal region to the apical region, the core comprising a core outer diameter that decreases at a core diameter decrease rate in an apical direction towards the apical end, the core diameter decrease rate being constant from the coronal region to the apical region;
   a prosthetic interface at the coronal region; and
   at least one thread extending around the core in a plurality of turns from the coronal region to the apical region, the at least one thread comprising a thread outer diameter configured to define a cylindrical portion, wherein the thread outer diameter remains constant for more than one turn around the core, and to define a conical portion, wherein the thread outer diameter decreases at a thread diameter decrease rate in the apical direction, the thread diameter decrease rate being greater than the core diameter decrease rate, wherein the cylindrical portion and the conical portion meet at an inflection point and thread height of the at least one thread is greater at turns adjacent the inflection point than turns adjacent the coronal and apical ends, thread height being a distance between the core and an outer face of the at least one thread, and wherein thread width of the at least one thread is greater at turns adjacent the coronal and apical ends than turns adjacent the inflection point, thread width being a distance between a coronal face of the at least one thread and an apical face of the at least one thread at the outer face.

2. The implant of claim 1, wherein the at least one thread comprises a plurality of curved notches each defining a cutting edge, the plurality of curved notches each partially notched to reflect a portion of a semi-spherical surface and partially notched to reflect a portion of a semi-cylindrical surface, the semi-spherical surface curving inward from apical and coronal edges that are curved, the semi-cylindrical surface curving inward from apical and coronal edges that are straight.

3. The implant of claim 1, wherein the at least one thread comprises a plurality of curved notches each defining a cutting edge, wherein a first curved notch on a first turn does not overlap with a second curved notch on a second turn by more than 10% a width of the first curved notch at one side of the first curved notch, the second turn being adjacent the first turn in a coronal direction, and wherein the first curved notch does not overlap with a third curved notch on a third turn by more than 10% the width of the first curved notch at an opposing side of the first curved notch, the third turn being adjacent the first turn in the apical direction.

4. The implant of claim 1, wherein the at least one thread comprises two threads extending around the core in a double-thread configuration.

5. The implant of claim 1, wherein the apical end has a rounded shape, the apical end extending beyond the at least one thread between 0.1 and 0.7 mm in the apical direction.

6. The implant of claim 1, wherein the coronal region adjacent the coronal end comprises one or more concave rings.

7. The implant of claim 1, wherein at least a portion of the coronal region has a frustoconical shape with decreasing size in a coronal direction.

8. The implant of claim 1, wherein the prosthetic interface comprises a Morse taper connection.

9. The implant of claim 1, wherein the prosthetic interface comprises an anti-rotation coupling in a hexagon shape.

10. The implant of claim 1, wherein the prosthetic interface is adapted for direct coupling to a bridge or crown.

11. An implant for anchoring within bone, the implant comprising:
a coronal region comprising a coronal end;
an apical region comprising an apical end, the apical end opposite the coronal end;
a core extending from the coronal region to the apical region;
a prosthetic interface at the coronal region; and
at least one thread extending around the core in a plurality of turns from the coronal region to the apical region, the at least one thread comprising a plurality of curved notches each defining a cutting edge, the plurality of curved notches each partially notched to reflect a portion of a semi-spherical surface and partially notched to reflect a portion of a semi-cylindrical surface, wherein the portion of the semi-spherical surface intersects with the portion of the semi-cylindrical surface in each of the plurality of curved notches, wherein a first curved notch on a first turn does not overlap with a second curved notch on a second turn by more than 10% a width of the first curved notch at one side of the first curved notch, the second turn being adjacent the first turn in a coronal direction, and wherein the first curved notch does not overlap with a third curved notch on a third turn by more than 10% the width of the first curved notch at an opposing side of the first curved notch, the third turn being adjacent the first turn in an apical direction.

12. The implant of claim 11, wherein the second turn is immediately adjacent the first turn in the coronal direction and the third turn is immediately adjacent the first turn in the apical direction.

13. The implant of claim 11, wherein the at least one thread comprises a thread outer diameter configured to define a cylindrical portion, wherein the thread outer diameter remains constant for more than one turn around the core, and to define a conical portion, wherein the thread outer diameter decreases at a thread diameter decrease rate in the apical direction, the thread diameter decrease rate being greater than a core diameter decrease rate.

14. The implant of claim 11, wherein the first curved notch does not overlap with the second curved notch and does not overlap with the third curved notch.

15. The implant of claim 11, wherein the at least one thread comprises two threads extending around the core in a double-thread configuration.

16. The implant of claim 11, wherein the coronal region adjacent the coronal end comprises one or more concave rings and, optionally, wherein at least a portion of the coronal region has a frustoconical shape with decreasing size in a coronal direction.

17. The implant of claim 11, wherein the prosthetic interface comprises a Morse taper connection or an anti-rotation coupling in a hexagon shape or is adapted for direct coupling to a bridge or crown.

18. An implant for anchoring within bone, the implant comprising:
a coronal region comprising a coronal end;
an apical region comprising an apical end, the apical end opposite the coronal end;
a core extending from the coronal region to the apical region;
a prosthetic interface at the coronal region; and
at least one thread extending around the core in a plurality of turns from the coronal region to the apical region, the at least one thread comprising a plurality of curved notches each defining a cutting edge,
wherein at least one of the plurality of curved notches is partially notched to reflect a portion of a semi-spherical surface and partially notched to reflect a portion of a semi-cylindrical surface, the semi-spherical surface defining apical and coronal edges that are curved.

19. The implant of claim 18, wherein the semi-spherical surface curves inward from the apical and coronal edges that are curved and the semi-cylindrical surface curves inward from apical and coronal edges that are straight.

20. The implant of claim 18, wherein each of the plurality of curved notches does not overlap by more than 50% a width of each curved notch with adjacent curved notches on adjacent turns.

21. The implant of claim 18, wherein the portion of the semi-spherical surface intersects with the portion of the semi-cylindrical surface in the at least one of the plurality of curved notches.

22. The implant of claim 18, wherein the at least one thread comprises a thread outer diameter configured to define a cylindrical portion, wherein the thread outer diameter remains constant for more than one turn around the core, and to define a conical portion, wherein the thread outer diameter decreases at a thread diameter decrease rate in the apical direction, the thread diameter decrease rate being greater than a core diameter decrease rate.

* * * * *